United States Patent
Jubran et al.

(10) Patent No.: US 7,094,510 B2
(45) Date of Patent: Aug. 22, 2006

(54) ORGANOPHOTORECEPTOR WITH A CHARGE TRANSPORT MATERIAL HAVING TWO (9-FLUORENYLIDENE)MALONONITRILE GROUPS

(75) Inventors: Nusrallah Jubran, St. Paul, MN (US); Zbigniew Tokarski, Woodbury, MN (US); Kam W. Law, Woodbury, MN (US); Eric Morrison, St. Paul, MN (US); Vytautas Getautis, Kaunas (LT); Vygintas Jankauskas, Vilnius (LT)

(73) Assignee: Samsung Electric Co., Ltd., Suwon (KR)

( * ) Notice: Subject to any disclaimer, the term of this patent is extended or adjusted under 35 U.S.C. 154(b) by 162 days.

(21) Appl. No.: 10/748,424

(22) Filed: Dec. 30, 2003

(65) Prior Publication Data

US 2004/0170909 A1     Sep. 2, 2004

Related U.S. Application Data

(60) Provisional application No. 60/451,304, filed on Feb. 28, 2003.

(51) Int. Cl.
  *G03G 5/06* (2006.01)
  *C07C 255/57* (2006.01)
(52) U.S. Cl. .................. 430/72; 430/75; 548/528; 558/395
(58) Field of Classification Search .................. 430/72, 430/75; 548/528; 558/395
  See application file for complete search history.

(56) References Cited

U.S. PATENT DOCUMENTS

| 4,047,949 A | 9/1977 | Horgan |
| 4,115,116 A | 9/1978 | Stolka et al. |
| 4,135,928 A | 1/1979 | Hashimoto et al. |
| 4,315,981 A | 2/1982 | Wiedemann |
| 4,474,865 A | 10/1984 | Ong et al. |
| 4,559,287 A | 12/1985 | McAneney et al. |
| 4,562,132 A | 12/1985 | Ong et al. |
| 4,835,081 A * | 5/1989 | Ong et al. ............... 430/58.25 |

FOREIGN PATENT DOCUMENTS

| EP | 1418469 A2 | 5/2004 |
| JP | 7056369 A | 3/1995 |
| JP | 9265198 A | 10/1997 |
| JP | 9316036 | 12/1997 |
| JP | 8062921 A2 | 3/1999 |
| JP | 2001-109764 | 4/2003 |
| JP | 2003-109763 | 4/2003 |
| WO | WO01/46757 A1 | 6/2001 |

OTHER PUBLICATIONS

"Electron Acceptors Derived from Fluorenecarboxylic Acids and Their Cahrge-Transfer Complex" by Theodore Sulzberg and Robert J. Cotter; Journal of Organic Chemistry, vol. 35, No. 8, pp. 2762-2769 (1970).

* cited by examiner

*Primary Examiner*—John L Goodrow
(74) *Attorney, Agent, or Firm*—Patterson, Thuente, Skaar & Christensen, P.A.

(57) ABSTRACT

Improved organophotoreceptor comprises an electrically conductive substrate and a photoconductive element on the electrically conductive substrate, the photoconductive element comprising:
  (a) a charge transport material having the formula

X-Z-X' where X and X' are, each independently, a (9-fluorenylidene)malononitrile group, and Z is a linking group; and
  (b) a charge generating compound.

Corresponding electrophotographic apparatuses and imaging methods are described.

22 Claims, No Drawings

ORGANOPHOTORECEPTOR WITH A CHARGE TRANSPORT MATERIAL HAVING TWO (9-FLUORENYLIDENE)MALONONITRILE GROUPS

CROSS REFERENCE TO RELATED APPLICATION

This application claims priority to copending U.S. Provisional Patent Application Ser. No. 60/451,304 filed Feb. 28, 2003 to Tokarski et al., entitled "Electrophotographic Organophotoreceptors With Novel Charge Transport Compounds," incorporated herein by reference.

FIELD OF THE INVENTION

This invention relates to organophotoreceptors suitable for use in electrophotography and, more specifically, to organophotoreceptors with a charge transport material having two (9-fluorenylidene)malononitrile groups.

BACKGROUND OF THE INVENTION

In electrophotography, an organophotoreceptor in the form of a plate, disk, sheet, belt, drum or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas where light strikes the surface, thereby forming a pattern of charged and uncharged areas, referred to as a latent image. A liquid or solid toner is then provided in the vicinity of the latent image, and toner droplets or particles deposit in the vicinity of either the charged or uncharged areas to create a toned image on the surface of the photoconductive layer. The resulting toned image can be transferred to a suitable ultimate or intermediate receiving surface, such as paper, or the photoconductive layer can operate as an ultimate receptor for the image. The imaging process can be repeated many times to complete a single image, for example, by overlaying images of distinct color components or effect shadow images, such as overlaying images of distinct colors to form a full color final image, and/or to reproduce additional images.

Both single layer and multilayer photoconductive elements have been used. In single layer embodiments, a charge transport material and charge generating material are combined with a polymeric binder and then deposited on the electrically conductive substrate. In multilayer embodiments, the charge transport material and charge generating material are present in the element in separate layers, each of which can optionally be combined with a polymeric binder, deposited on the electrically conductive substrate. Two arrangements are possible for a two-layer photoconductive element. In one two-layer arrangement (the "dual layer" arrangement), the charge-generating layer is deposited on the electrically conductive substrate and the charge transport layer is deposited on top of the charge generating layer. In an alternate two-layer arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport material is to accept at least one type of these charge carriers and transport them through the charge transport layer in order to facilitate discharge of a surface charge on the photoconductive element. The charge transport material can be a charge transport compound, an electron transport compound, or a combination of both. When a charge transport compound is used, the charge transport compound accepts the hole carriers and transports them through the layer with the charge transport compound. When an electron transport compound is used, the electron transport compound accepts the electron carriers, and transports them through the layer with the electron transport compound.

SUMMARY OF THE INVENTION

This invention provides organophotoreceptors having good electrostatic properties such as high $V_{acc}$ and low $V_{dis}$.

In a first aspect, an organophotoreceptor comprises an electrically conductive substrate and a photoconductive element on the electrically conductive substrate, the photoconductive element comprising:

(a) a charge transport material having the formula

X-Z-X' where X and X' are, each independently, a (9-fluorenylidene)malononitrile group, and Z is a linking group having the formula —$(CH_2)_m$—, branched or linear, where m is an integer between 1 and 30, inclusive, and one or more of the methylene groups may be replaced by O, S, C=O, Si=O, S(=O)$_2$, P(=O)$_2$, an aromatic group, a heterocyclic group, an aliphatic cyclic group, a Si($R_1$)($R_2$) group, a $BR_3$ group, a $NR_4$ group, a $CHR_5$ group, or a $CR_6R_7$ group where $R_1$, $R_2$, $R_3$, $R_4$, $R_5$, $R_6$, and $R_7$ are, each independently, H, halogen, hydroxyl, thiol, an alkoxy group, an alkyl group, an alkenyl group, an aromatic group, a heterocyclic group, or a part of a cyclic ring; and (b) a charge generating compound.

The organophotoreceptor may be provided, for example, in the form of a plate, a flexible belt, a flexible disk, a sheet, a rigid drum, or a sheet around a rigid or compliant drum. In one embodiment, the organophotoreceptor includes: (a) a photoconductive element comprising the charge transport material, the charge generating compound, a second charge transport material, and a polymeric binder; and (b) the electrically conductive substrate.

In a second aspect, the invention features an electrophotographic imaging apparatus that comprises (a) a light imaging component; and (b) the above-described organophotoreceptor oriented to receive light from the light imaging component. The apparatus can further comprise a liquid toner dispenser. The method of electrophotographic imaging with photoreceptors containing the above noted charge transport materials is also described.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of at least relatively charged and uncharged areas on the surface; (c) contacting the surface with a toner, such as a liquid toner that includes a dispersion of colorant particles in an organic liquid, to create a toned image; and (d) transferring the toned image to a substrate.

In a fourth aspect, the invention features a charge transport material having the general formula above.

The invention provides suitable charge transport materials for organophotoreceptors featuring a combination of good mechanical and electrostatic properties. These photoreceptors can be used successfully with liquid toners to produce high quality images. The high quality of the imaging system can be maintained after repeated cycling.

Other features and advantages of the invention will be apparent from the following description of the particular embodiments thereof, and from the claims.

DETAILED DESCRIPTION OF PREFERRED EMBODIMENTS

An organophotoreceptor as described herein has an electrically conductive substrate and a photoconductive element comprising a charge generating compound and a charge transport material having two (9-fluorenylidene)malononitrile groups linked together by a linking group. The two (9-fluorenylidene)malononitrile groups may be the same or different. These charge transport materials have desirable properties as evidenced by their performance in organophotoreceptors for electrophotography. In particular, the charge transport materials of this invention have high charge carrier mobilities and good compatibility with various binder materials, and possess excellent electrophotographic properties. The organophotoreceptors according to this invention generally have a high photosensitivity, a low residual potential, and a high stability with respect to cycle testing, crystallization, and organophotoreceptor bending and stretching. The organophotoreceptors are particularly useful in laser printers and the like as well as fax machines, photocopiers, scanners and other electronic devices based on electrophotography. The use of these charge transport materials is described in more detail below in the context of laser printer use, although their application in other devices operating by electrophotography can be generalized from the discussion below.

To produce high quality images, particularly after multiple cycles, it is desirable for the charge transport materials to form a homogeneous solution with the polymeric binder and remain approximately homogeneously distributed through the organophotoreceptor material during the cycling of the material. In addition, it is desirable to increase the amount of charge that the charge transport material can accept (indicated by a parameter known as the acceptance voltage or "$V_{acc}$"), and to reduce retention of that charge upon discharge (indicated by a parameter known as the discharge voltage or "$V_{dis}$").

The charge transport materials can be classified as a charge transport compound or an electron transport compound. There are many charge transport compounds and electron transport compounds known in the art for electrophotography. Non-limiting examples of charge transport compounds include, for example, pyrazoline derivatives, fluorene derivatives, oxadiazole derivatives, stilbene derivatives, enamine derivatives, enamine stilbene derivatives, hydrazone derivatives, carbazole hydrazone derivatives, (N,N-disubstituted)arylamines such as triaryl amines, polyvinyl carbazole, polyvinyl pyrene, polyacenaphthylene, or multi-hydrazone compounds comprising at least two hydrazone groups and at least two groups selected from the group consisting of (N,N-disubstituted)arylamine such as triphenylamine and heterocycles such as carbazole, julolidine, phenothiazine, phenazine, phenoxazine, phenoxathiin, thiazole, oxazole, isoxazole, dibenzo(1,4)dioxin, thianthrene, imidazole, benzothiazole, benzotriazole, benzoxazole, benzimidazole, quinoline, isoquinoline, quinoxaline, indole, indazole, pyrrole, purine, pyridine, pyridazine, pyrimidine, pyrazine, triazole, oxadiazole, tetrazole, thiadiazole, benzisoxazole, benzisothiazole, dibenzofuran, dibenzothiophene, thiophene, thianaphthene, quinazoline, or cinnoline.

Non-limiting examples of electron transport compounds include, for example, bromoaniline, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno[1,2-b]thiophene-4-one, and 1,3,7-trinitrodibenzothiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethylidene) thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenylidene)malononitrile, (4-carbitoxy-9-fluorenylidene)malononitrile, and diethyl(4-n-butoxycarbonyl-2,7-dinitro-9-fluorenylidene)-malonate, anthraquinodimethane derivatives such as 11,11,12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxy carbonyl) methylene]anthrone, 1,8-dihydroxy-10-[bis(ethoxycarbonyl)methylene] anthrone, and 1-cyano-10-[bis (ethoxycarbonyl)methylene)anthrone, 7-nitro-2-aza-9-fluoenylidene-malononitrile, diphenoquinone derivatives, benzoquinone derivatives, naphtoquinone derivatives, quinine derivatives, tetracyanoethylenecyanoethylene, 2,4,8-trinitro thioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenylmethane derivatives, tetracyano quinoedimethane, 2,4,5,7-tetranitro-9-fluorenone, 2,4,7-trinitro-9-dicyanomethylene fluorenone, 2,4,5,7-tetranitroxanthone derivatives, and 2,4,8-trinitrothioxanthone derivatives. In some embodiments of interest, the electron transport compound comprises an (alkoxycarbonyl-9-fluorenylidene)malononitrile derivative, such as (4-n-butoxycarbonyl-9-fluorenylidene) malononitrile.

Although there are many charge transport materials available, there is a need for other charge transport materials to meet the various requirements of particular electrophotography applications.

In electrophotography applications, a charge-generating compound within an organophotoreceptor absorbs light to form electron-hole pairs. These electrons and holes can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport materials described herein are especially effective at transporting charge, and in particular holes from the electron-hole pairs formed by the charge generating compound. In some embodiments, a specific electron transport compound or charge transport compound can also be used along with the charge transport material of this invention.

The layer or layers of materials containing the charge generating compound and the charge transport materials are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport material can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport material and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport material and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the entire surface is discharged, and the material is ready to cycle again. The imaging apparatus can further comprise, for example, a plurality of support rollers for transporting a paper receiving medium and/or for movement of the photoreceptor, a light imaging component with suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

As described herein, an organophotoreceptor comprises a charge transport material having the formula

where X and X' are, each independently, a (9-fluorenylidene)malononitrile group, and Z is a linking group having the formula —$(CH_2)_m$—, branched or linear, where m is an integer between 1 and 30, inclusive, and one or more of the methylene groups may be replaced by O, S, C=O, Si=O, S(=O)$_2$, P(=O)$_2$, an aromatic group, a heterocyclic group, an aliphatic cyclic group, a Si($R_1$)($R_2$) group, a $BR_3$ group, a $NR_4$ group, a $CHR_5$ group, or a $CR_6R_7$ group where $R_1$, $R_2$, $R_3$, $R_4$, $R_5$, $R_6$, and $R_7$ are, each independently, H, halogen, hydroxyl, thiol, an alkoxy group, an alkyl group, an alkenyl group, an aromatic group, a heterocyclic group, or a part of a cyclic ring.

The aromatic group can be any conjugated system containing 4n+2 π-electrons. There are many criteria available for determining aromaticity. A widely employed criterion for the quantitative assessment of aromaticity is the resonance energy. In general, the resonance energy of the aromatic group is greater than 10 KJ/mol. Aromatic groups may be classified as an aromatic heterocyclic group which contains at least a heteroatom in the 4n+2 π-electron ring, or as an aryl group which does not contain a heteroatom in the 4n+2 π-electron ring. Nonetheless, either the aromatic heterocyclic or the aryl group may have at least one heteroatom in a substituent attached to the 4n+2 π-electron ring. Furthermore, either the aromatic heterocyclic or the aryl group may comprise a monocyclic or polycyclic (such as bicyclic, tricyclic, etc.) aromatic ring.

Non-limiting examples of the aromatic heterocyclic group are furanyl, thiophenyl, pyrrolyl, indolyl, carbazolyl, benzofuranyl, benzothiophenyl, dibenzofuranyl, dibenzothiophenyl, pyridinyl, pyridazinyl, pyrimidinyl, pyrazinyl, triazinyl, tetrazinyl, petazinyl, quinolinyl, isoquinolinyl, cinnolinyl, phthalazinyl, quinazolinyl, quinoxalinyl, naphthyridinyl, pteridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4)dioxinyl, thianthrenyl, and a combination thereof. The aromatic heterocyclic group may also include any combination of the above aromatic heterocyclic groups bonded together either by a bond (as in bicarbazolyl) or by a linking group (as in 1,6-di(10H-10-phenothiazinyl)hexane). The linking group may include an aliphatic group, an aromatic group, a heterocyclic group, or a combination thereof. Furthermore, either an aliphatic group or an aromatic group within a linking group may comprise at least one heteroatom such as O, S, and N.

Non-limiting examples of the aryl group are phenyl, naphthyl, benzyl, or tolanyl group, sexiphenylene, phenanthrenyl, anthracenyl, coronenyl, and tolanylphenyl. The aryl group may also include any combination of the above aryl groups bonded together either by a bond (as in biphenyl group) or by a linking group (as in stilbenyl, diphenyl sulfone, an arylamine group). The linking group may include an aliphatic group, an aromatic group, a heterocyclic group, or a combination thereof. Furthermore, either an aliphatic group or an aromatic group within a linking group may comprise at least one heteroatom such as O, S, and N.

A (9-fluorenylidene)malononitrile group has the following formula

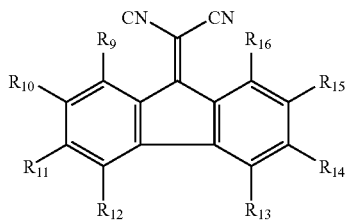

where $R_9$, $R_{10}$, $R_{11}$, $R_{12}$, $R_{13}$, $R_{14}$, $R_{15}$, and $R_{16}$ are, each independently, a bond, H, halogen, hydroxyl, amino, thiol, an alkoxy group, an alkyl group, an alkenyl group, an aromatic group, a heterocyclic group, or a part of a cyclic ring. Upon incorporation into the charge transport material, one of the $R_9$–$R_{15}$ groups is joined to the linking group.

Substitution is liberally allowed on the chemical groups to affect various physical effects on the properties of the compounds, such as mobility, sensitivity, solubility, stability, and the like, as is known generally in the art. In the description of chemical substituents, there are certain practices common to the art that are reflected in the use of language. The term group indicates that the generically recited chemical entity (e.g., alkyl group, phenyl group, aromatic group, heterocyclic group, (9-fluorenylidene)malononitrile group, etc.) may have any substituent thereon which is consistent with the bond structure of that group. For example, where the term 'alkyl group' is used, that term would not only include unsubstituted linear, branched and cyclic alkyls, such as methyl, ethyl, isopropyl, tert-butyl, cyclohexyl, dodecyl and the like, but also substituents having heteroatom such as 3-ethoxylpropyl, 4-(N-ethylamino)butyl, 3-hydroxypentyl, 2-thiolhexyl, 1,2,3-tribromoopropyl, and the like. However, as is consistent with such nomenclature, no substitution would be included within the term that would alter the fundamental bond structure of the underlying group. When referring to an aromatic group, the substituent cited can include any substitution that does not decrease the resonance energy of the aromatic group to less than 10 KJ/mol. For example, where a phenyl group is recited, substitution such as 1-aminophenyl, 2,4-dihydroxyphenyl, 1,3,5-trithiophenyl, 1,3,5-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form. When referring to a (9-fluorenylidene)malononitrile group, the substituent cited will include any substitution that does not substantively alter the chemical nature, such as aromaticity, conjugation, and the ability to transfer electrons or holes, of the (9-fluorenylidene)malononitrile group. Where the term moiety is used, such as alkyl moiety or phenyl moiety, that terminology indicates that the chemical material is not substituted. Where the term alkyl moiety is used, that term represents only an unsubstituted alkyl hydrocarbon group, whether branched, straight chain, or cyclic.

Organophotorecptors

The organophotoreceptor may be, for example, in the form of a plate, a sheet, a flexible belt, a disk, a rigid drum, or a sheet around a rigid or compliant drum, with flexible belts and rigid drums generally being used in commercial embodiments. The organophotoreceptor may comprise, for example, an electrically conductive substrate and on the electrically conductive substrate a photoconductive element in the form of one or more layers. The photoconductive element can comprise both a charge transport material and a charge generating compound in a polymeric binder, which may or may not be in the same layer, as well as a second charge transport material such as a charge transport compound or an electron transport compound in some embodiments. For example, the charge transport material and the charge generating compound can be in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyester (e.g., polyethylene terephthalate or polyethylene naphthalate), polyimide, polysulfone, polypropylene, nylon, polyester, polycarbonate, polyvinyl resin, polyvinyl fluoride, polystyrene and the like. Specific examples of polymers for supporting substrates included, for example, polyethersulfone (Stabar™ S-100, available from ICI), polyvinyl fluoride (Tedlar™, available from E. I. DuPont de Nemours & Company), polybisphenol-A polycarbonate (Makrofol™, available from Mobay Chemical Company) and amorphous polyethylene terephthalate (Melinar™, available from ICI Americas, Inc.). The electrically conductive materials may be graphite, dispersed carbon black, iodine, conductive polymers such as polypyrroles and Calgon™ conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate has a thickness adequate to provide the required mechanical stability. For example, flexible web substrates generally have a thickness from about 0.01 to about 1 mm, while drum substrates generally have a thickness from about 0.5 mm to about 2 mm.

The charge generating compound is a material that is capable of absorbing light to generate charge carriers, such as a dye or pigment. Non-limiting examples of suitable charge generating compounds include, for example, metal-free phthalocyanines (e.g., ELA 8034 metal-free phthalocyanine available from H. W. Sands, Inc. or Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound), hydroxygallium phthalocyanine, squarylium dyes and pigments, hydroxy-substituted squarylium pigments, perylimides, polynuclear quinones available from Allied Chemical Corporation under the trade name Indofast® Double Scarlet, Indofast® Violet Lake B, Indofast® Brilliant Scarlet and Indofast® Orange, quinacridones available from DuPont under the trade name Monastral™ Red, Monastral™ Violet and Monastral™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmium selenide, cadmium sulphide, and mixtures thereof. For some embodiments, the charge generating compound comprises oxytitanium phthalocyanine (e.g., any phase thereof), hydroxygallium phthalocyanine or a combination thereof.

The photoconductive layer of this invention may optionally contain a second charge transport material which may be a charge transport compound, an electron transport compound, or a combination of both. Generally, any charge transport compound or electron transport compound known in the art can be used as the second charge transport material.

An electron transport compound and a UV light stabilizer can have a synergistic relationship for providing desired electron flow within the photoconductor. The presence of the UV light stabilizers alters the electron transport properties of the electron transport compounds to improve the electron transporting properties of the composite. UV light stabilizers can be ultraviolet light absorbers or ultraviolet light inhibitors that trap free radicals.

UV light absorbers can absorb ultraviolet radiation and dissipate it as heat. UV light inhibitors are thought to trap free radicals generated by the ultraviolet light and after trapping of the free radicals, subsequently to regenerate active stabilizer moieties with energy dissipation. In view of the synergistic relationship of the UV stabilizers with electron transport compounds, the particular advantages of the UV stabilizers may not be their UV stabilizing abilities, although the UV stabilizing ability may be further advantageous in reducing degradation of the organophotoreceptor over time. The improved synergistic performance of organophotoreceptors with layers comprising both an electron transport compound and a UV stabilizer are described further in copending U.S. patent application Ser. No. 10/425,333 filed on Apr. 28, 2003 to Zhu, entitled "Organophotoreceptor With A Light Stabilizer," incorporated herein by reference.

Non-limiting examples of suitable light stabilizer include, for example, hindered trialkylamines such as Tinuvin 144 and Tinuvin 292 (from Ciba Specialty Chemicals, Terrytown, N.Y.), hindered alkoxydialkylamines such as Tinuvin 123 (from Ciba Specialty Chemicals), benzotriazoles such as Tinuvan 328, Tinuvin 900 and Tinuvin 928 (from Ciba Specialty Chemicals), benzophenones such as Sanduvor 3041 (from Clariant Corp., Charlotte, N.C.), nickel compounds such as Arbestab (from Robinson Brothers Ltd, West Midlands, Great Britain), salicylates, cyanocinnamates, benzylidene malonates, benzoates, oxanilides such as Sanduvor VSU (from Clariant Corp., Charlotte, N.C.), triazines such as Cyagard UV-1164 (from Cytec Industries Inc., N.J.), polymeric sterically hindered amines such as Luchem (from Atochem North America, Buffalo, N.Y.). In some embodiments, the light stabilizer is selected from the group consisting of hindered trialkylamines having the following formula:

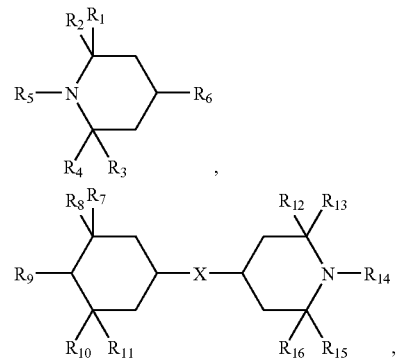

where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, each independently, hydrogen, alkyl group, or ester, or ether group; and $R_5$, $R_9$, and $R_{14}$ are, each independently, alkyl group; and X is a linking group selected from the group consisting of —O—CO—$(CH_2)_m$—CO—O— where m is between 2 to 20.

The binder generally is capable of dispersing or dissolving the charge transport material (in the case of the charge transport layer or a single layer construction), the charge generating compound (in the case of the charge generating layer or a single layer construction) and/or an electron transport compound for appropriate embodiments. Examples of suitable binders for both the charge generating layer and charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak, poly(phenylglycidyl ether)-co-dicyclopentadiene, copolymers of monomers used in the above-mentioned polymers, and combinations thereof. Specific suitable binders include, for example, polyvinyl butyral, polycarbonate, and polyester. Non-limiting examples of polyvinyl butyral include BX-1 and BX-5 from Sekisui Chemical Co. Ltd., Japan. Non-limiting examples of suitable polycarbonate include polycarbonate A which is derived from bisphenol-A (e.g. Iupilon-A from Mitsubishi Engineering Plastics, or Lexan 145 from General Electric); polycarbonate Z which is derived from cyclohexylidene bisphenol (e.g. Iupilon-Z from Mitsubishi Engineering Plastics Corp, White Plain, N.Y.); and polycarbonate C which is derived from methylbisphenol A (from Mitsubishi Chemical Corporation). Non-limiting examples of suitable polyester binders include ortho-polyethylene terephthalate (e.g. OPET TR-4 from Kanebo Ltd., Yamaguchi, Japan).

Suitable optional additives for any one or more of the layers include, for example, antioxidants, coupling agents, dispersing agents, curing agents, surfactants, and combinations thereof.

The photoconductive element overall typically has a thickness from about 10 microns to about 45 microns. In the dual layer embodiments having a separate charge generating layer and a separate charge transport layer, charge generation layer generally has a thickness form about 0.5 microns to about 2 microns, and the charge transport layer has a thickness from about 5 microns to about 35 microns. In embodiments in which the charge transport material and the charge generating compound are in the same layer, the layer with the charge generating compound and the charge transport composition generally has a thickness from about 7 microns to about 30 microns. In embodiments with a distinct electron transport layer, the electron transport layer has an average thickness from about 0.5 microns to about 10 microns and in further embodiments from about 1 micron to about 3 microns. In general, an electron transport overcoat layer can increase mechanical abrasion resistance, increases resistance to carrier liquid and atmospheric moisture, and decreases degradation of the photoreceptor by corona gases. A person of ordinary skill in the art will recognize that additional ranges of thickness within the explicit ranges above are contemplated and are within the present disclosure.

Generally, for the organophotoreceptors described herein, the charge generation compound is in an amount from about 0.5 to about 25 weight percent in further embodiments in an amount from about 1 to about 15 weight percent and in other embodiments in an amount from about 2 to about 10 weight percent, based on the weight of the photoconductive layer. The charge transport material is in an amount from about 10 to about 80 weight percent, based on the weight of the photoconductive layer, in further embodiments in an amount from about 35 to about 60 weight percent, and in other embodiments from about 45 to about 55 weight percent, based on the weight of the photoconductive layer. The optional second charge transport material, when present, can be in an amount of at least about 2 weight percent, in other embodiments from about 2.5 to about 25 weight percent, based on the weight of the photoconductive layer, and in further embodiments in an amount from about 4 to about 20 weight percent, based on the weight of the photoconductive layer. The binder is in an amount from about 15 to about 80 weight percent, based on the weight of the photoconductive layer, and in further embodiments in an amount from about 20 to about 75 weight percent, based on the weight of the photoconductive layer. A person of ordinary skill in the art will recognize that additional ranges within the explicit ranges of compositions are contemplated and are within the present disclosure.

For the dual layer embodiments with a separate charge generating layer and a charge transport layer, the charge generation layer generally comprises a binder in an amount from about 10 to about 90 weight percent, in further embodiments from about 15 to about 80 weight percent and in some embodiments in an amount from about 20 to about 75 weight percent, based on the weight of the charge generation layer. The optional charge transport material in the charge generating layer, if present, generally can be in an amount of at least about 2.5 weight percent, in further embodiments from about 4 to about 30 weight percent and in other embodiments in an amount from about 10 to about 25 weight percent, based on the weight of the charge generating layer. The charge transport layer generally comprises a binder in an amount from about 20 weight percent to about 70 weight percent and in further embodiments in an amount from about 30 weight percent to about 50 weight percent. A person of ordinary skill in the art will recognize that additional ranges of binder concentrations for the dual layer embodiments within the explicit ranges above are contemplated and are within the present disclosure.

For the embodiments with a single layer having a charge generating compound and a charge transport material, the photoconductive layer generally comprises a binder, a charge transport material, and a charge generation compound. The charge generation compound can be in an amount from about 0.05 to about 25 weight percent and in further embodiment in an amount from about 2 to about 15 weight percent, based on the weight of the photoconductive layer. The charge transport material can be in an amount from about 10 to about 80 weight percent, in other embodiments from about 25 to about 65 weight percent, in additional embodiments from about 30 to about 60 weight percent and in further embodiments in an amount from about 35 to about 55 weight percent, based on the weight of the photoconductive layer, with the remainder of the photoconductive layer comprising the binder, and optionally additives, such as any conventional additives. A single layer with a charge transport composition and a charge generating compound generally comprises a binder in an amount from about 10 weight percent to about 75 weight percent, in other embodiments from about 20 weight percent to about 60 weight percent, and in further embodiments from about 25 weight percent to about 50 weight percent. Optionally, the layer with the charge generating compound and the charge transport material may comprise a second charge transport material. The optional second charge transport material, if present, generally can be in an amount of at least about 2.5 weight percent, in further embodiments from about 4 to about 30 weight percent and in other embodiments in an amount from about 10 to about 25 weight percent, based on the weight of the photoconductive layer. A person of ordinary skill in the art will recognize that additional composition ranges within the explicit compositions ranges for the layers above are contemplated and are within the present disclosure.

In general, any layer with an electron transport layer can advantageously further include a UV light stabilizer. In particular, the electron transport layer generally can comprise an electron transport compound, a binder, and an optional UV light stabilizer. An overcoat layer comprising an electron transport compound is described further in copending U.S. patent application Ser. No. 10/396,536 to Zhu et al. entitled, "Organophotoreceptor With An Electron Transport Layer," incorporated herein by reference. For example, an electron transport compound as described above may be used in the release layer of the photoconductors described herein. The electron transport compound in an electron transport layer can be in an amount from about 10 to about 50 weight percent, and in other embodiments in an amount from about 20 to about 40 weight percent, based on the weight of the electron transport layer. A person of ordinary skill in the art will recognize that additional ranges of compositions within the explicit ranges are contemplated and are within the present disclosure.

The UV light stabilizer, if present, in any one or more appropriate layers of the photoconductor generally is in an amount from about 0.5 to about 25 weight percent and in some embodiments in an amount from about 1 to about 10 weight percent, based on the weight of the particular layer. A person of ordinary skill in the art will recognize that additional ranges of compositions within the explicit ranges are contemplated and are within the present disclosure.

For example, the photoconductive layer may be formed by dispersing or dissolving the components, such as one or more of a charge generating compound, the charge transport material of this invention, a second charge transport material such as a charge transport compound or an electron transport compound, a UV light stabilizer, and a polymeric binder in organic solvent, coating the dispersion and/or solution on the respective underlying layer and drying the coating. In particular, the components can be dispersed by high shear homogenization, ball-milling, attritor milling, high energy bead (sand) milling or other size reduction processes or mixing means known in the art for effecting particle size reduction in forming a dispersion.

The photoreceptor may optionally have one or more additional layers as well. An additional layer can be, for example, a sub-layer or an overcoat layer, such as a barrier layer, a release layer, a protective layer, or an adhesive layer. A release layer or a protective layer may form the uppermost layer of the photoconductor element. A barrier layer may be sandwiched between the release layer and the photoconductive element or used to overcoat the photoconductive element. The barrier layer provides protection from abrasion to the underlayers. An adhesive layer locates and improves the adhesion between a photoconductive element, a barrier layer and a release layer, or any combination thereof. A sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked polymers.

The release layer may comprise, for example, any release layer composition known in the art. In some embodiments, the release layer comprises a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In further embodiments, the release layers comprise crosslinked polymers.

The protective layer can protect the organophotoreceptor from chemical and mechanical degradation. The protective layer may comprise any protective layer composition known in the art. In some embodiments, the protective layer is a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In some embodiments of particular interest, the release layers are crosslinked polymers.

An overcoat layer may comprise an electron transport compound as described further in copending U.S. patent application Ser. No. 10/396,536, filed on Mar. 25, 2003 to Zhu et al. entitled, "Organoreceptor With An Electron Transport Layer," incorporated herein by reference. For example, an electron transport compound, as described above, may be used in the release layer of this invention. The electron transport compound in the overcoat layer can be in an amount from about 2 to about 50 weight percent, and in other embodiments in an amount from about 10 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrrolidone, polyurethane, polymethyl methacrylate, poly(hydroxy amino ether) and the like. Barrier and adhesive layers are described further in U.S. Pat. No. 6,180,305 to Ackley et al., entitled "Organic Photoreceptors for Liquid Electrophotography," incorporated herein by reference.

Sub-layers can comprise, for example, polyvinylbutyral, organosilanes, hydrolyzable silanes, epoxy resins, polyesters, polyamides, polyurethanes, and the like. In some embodiments, the sub-layer has a dry thickness between about 20 Angstroms and about 2,000 Angstroms. Sublayers containing metal oxide conductive particles can be between about 1 and about 25 microns thick. A person of ordinary skill in the art will recognize that additional ranges of compositions and thickness within the explicit ranges are contemplated and are within the present disclosure.

The charge transport materials as described herein, and photoreceptors including these compounds, are suitable for use in an imaging process with either dry or liquid toner development. For example, any dry toners and liquid toners known in the art may be used in the process and the apparatus of this invention. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 1:1 to 10:1, and in other embodiments, from 4:1 to 8:1. Liquid toners are described further in Published U.S. patent applications Ser. No. 2002/0128349, entitled "Liquid Inks Comprising A Stable Organosol," 2002/0086916, entitled "Liquid Inks Comprising Treated Colorant Particles," and 2002/0197552, entitled "Phase Change Developer For Liquid Electrophotography," all three of which are incorporated herein by reference.

Charge Transport Material

As described herein, an organophotoreceptor comprises a charge transport material having the formula $$X-Z-X' \quad (1)$$

where X and X' are, each independently, a (9-fluorenylidene)malononitrile group, and Z is a linking group having the formula $—(CH_2)_m—$, branched or linear, where m is an integer between 1 and 30, inclusive, and one or more of the methylene groups may be replaced by O, S, C=O, Si=O, S(=O)$_2$, P(=O)$_2$, an aromatic group, a heterocyclic group, an aliphatic cyclic group, a Si(R$_1$)(R$_2$) group, a BR$_3$ group, a NR$_4$ group, a CHR$_5$ group, or a CR$_6$R$_7$ group where R$_1$, R$_2$, R$_3$, R$_4$, R$_5$, R$_6$, and R$_7$ are, each independently, H, halogen, hydroxyl, thiol, an alkoxy group, an alkyl group, an alkenyl group, an aromatic group, a heterocyclic group, or a part of a cyclic ring.

(9-Fluorenylidene)malononitrile groups X and X' may be the same or different. Furthermore, the (9-fluorenylidene)malononitrile group may have at least a substituent such as halogen, nitro group, and cyano group. Specific, non-limiting examples of suitable charge transport materials within the general Formula (1) of the present invention have the following structures:

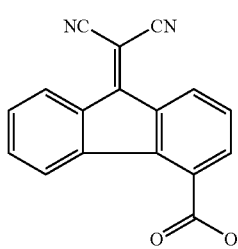
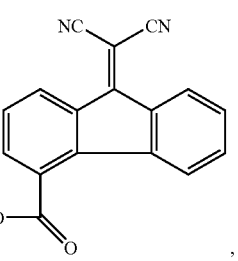

(2)

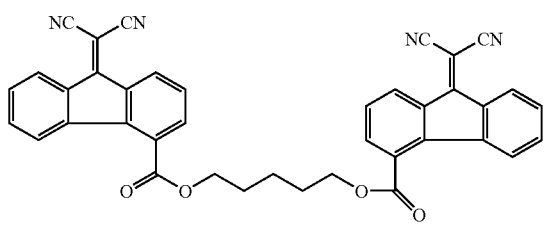

(3)

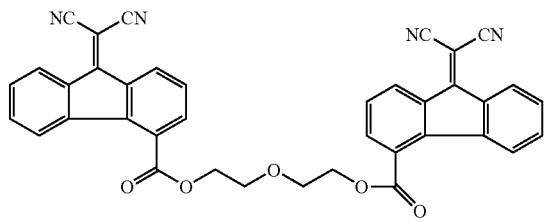

(4)

(5)

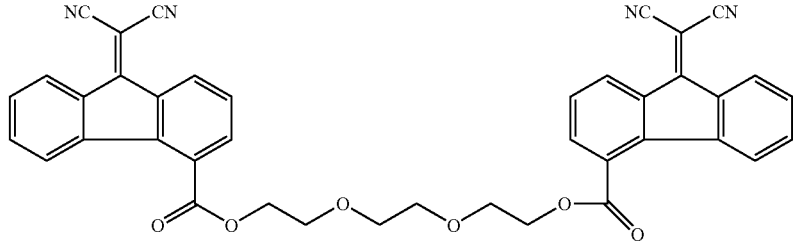

(6)

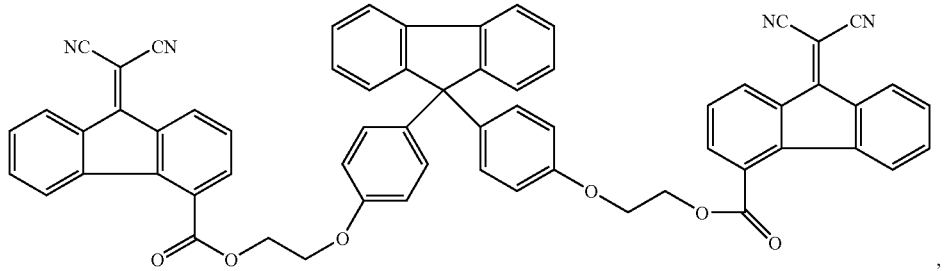

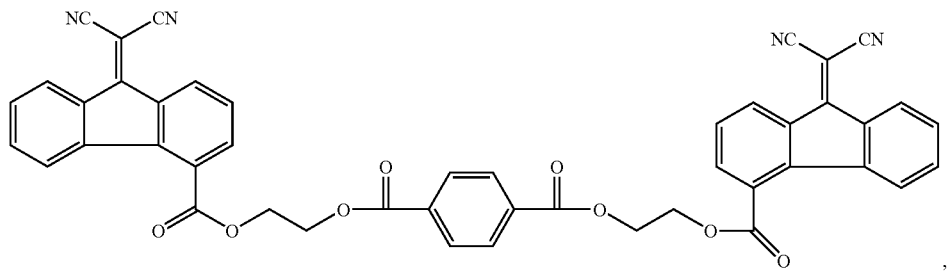
(7)
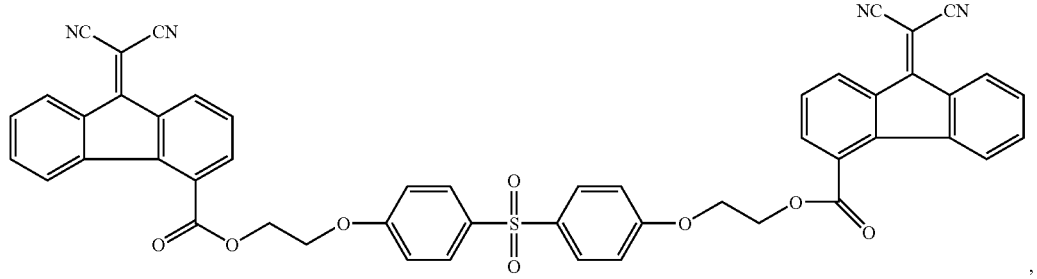
(8)
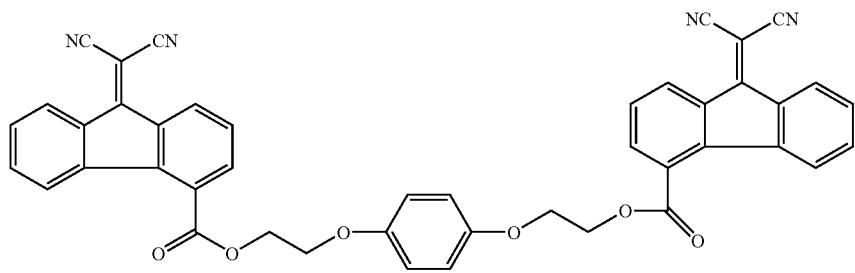
(9)
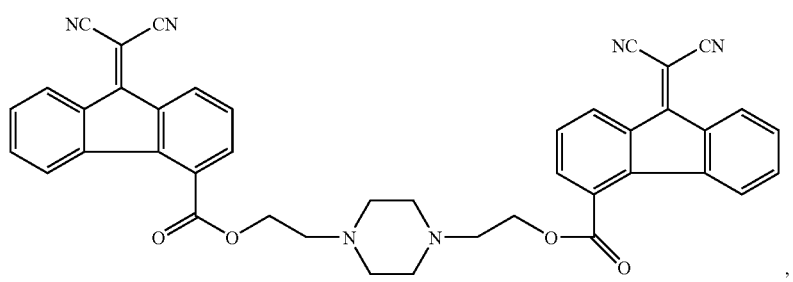
(10)
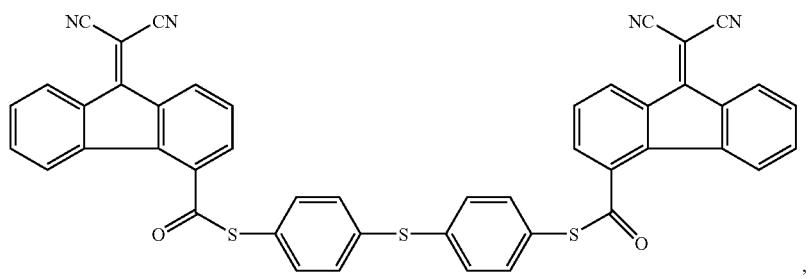
(11)

-continued
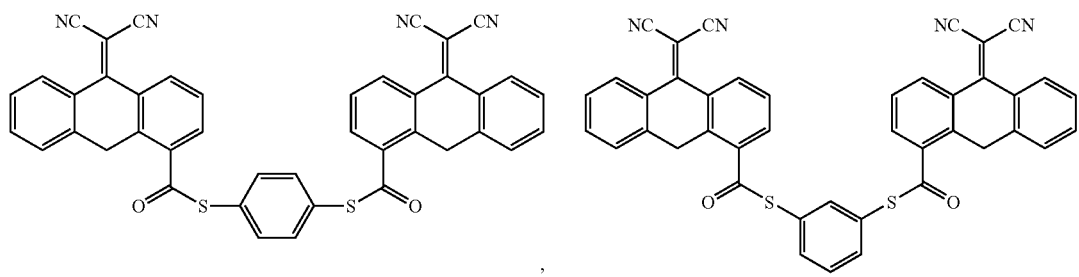
(12)
(13)
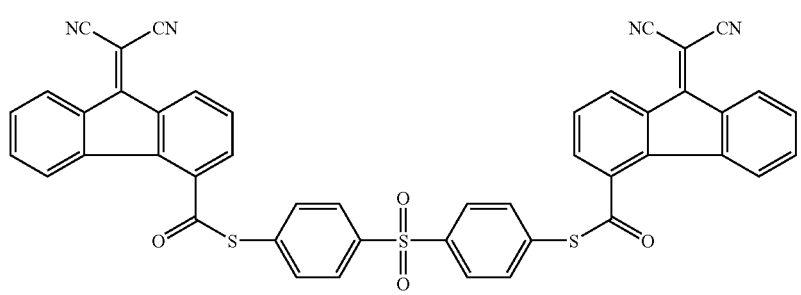
(14)
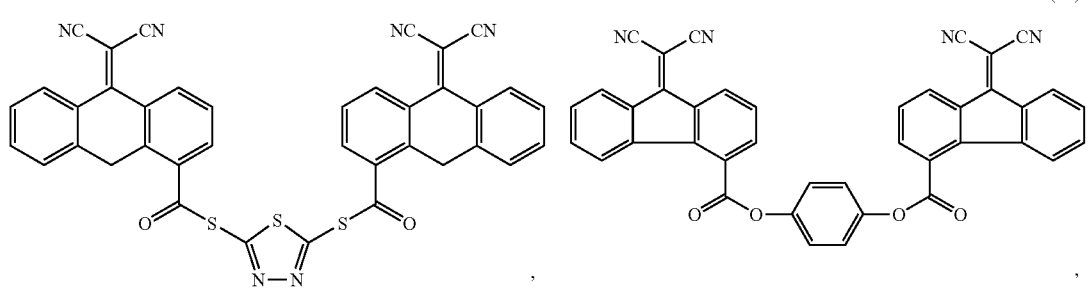
(15)
(16)
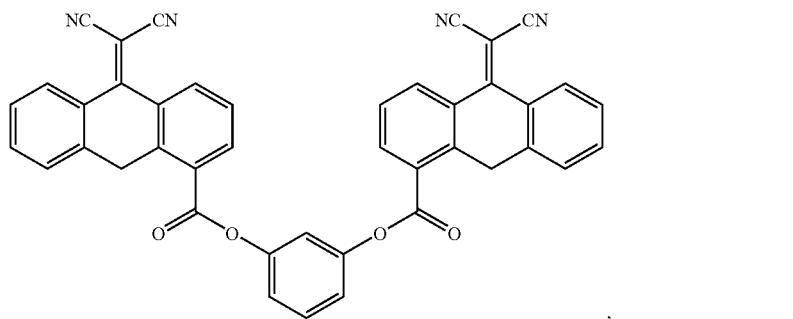
(17)
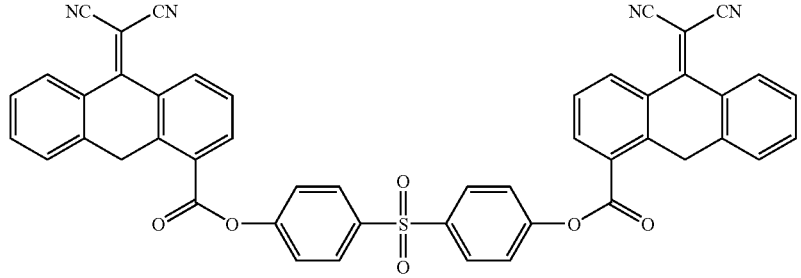
(18)
, and

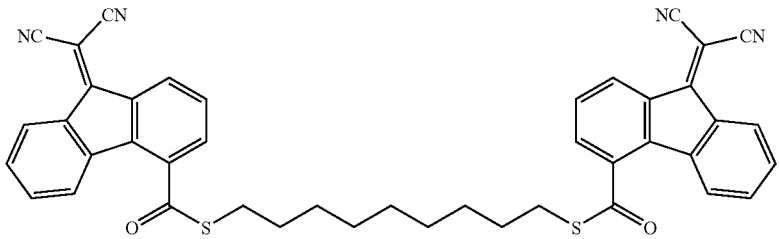

(19)

Synthesis Of Charge Transport Materials

The synthesis of the charge transport materials of this invention can be prepared by the following multi-step synthetic procedures, although other suitable procedures can be used by a person of ordinary skill in the art based on the disclosure herein.

The following steps are suitable for synthesizing some charge transport materials of this invention involving a linking reaction as described in the following. In the first step, diphenic acid or its derivative is dissolved in large access of concentrated sulfuric acid and the solution is heated at approximately 70° C. for about 10 minutes. The product, 9-fluorenone-4-carboxylic acid or its derivative, is isolated. In the second step, 9-fluorenone-4-carboxylic acid or its derivative is chlorinated with thionyl chloride to form 9-fluorenone-4-carbonyl chloride or its derivative. Then, 9-fluorenone-4-carbonyl chloride or its derivative reacts with a diol, a dithiol, a diamine, a hydroxylamine, a hydroxythiol, or a thioamine in the presence of triethylamine. Non-limiting examples of suitable dithiol are 4,4'-thiobisbenzenethiol, 1,4-benzenedithiol, 1,3-benzenedithiol, sulfonyl-bis(benzenethiol), 2,5-dimecapto-1,3,4-thiadiazole, 1,2-ethanedithiol, 1,3-propanedithiol, 1,4-butanedithiol, 1,5-pentanedithiol, and 1,6-hexanedithiol. Non-limiting examples of suitable diols are 2,2'-bi-7-naphtol, 1,4-dihydroxybenzene, 1,3-dihydroxybenzene, 10,10-bis(4-hydroxyphenyl)anthrone, 4,4'-sulfonyldiphenol, bisphenol, 4,4'-(9-fluorenylidene)diphenol, 1,10-decanediol, 1,5-pentanediol, diethylene glycol, 4.4'-(9-fluorenylidene)-bis(2-phenoxyethanol), bis(2-hydroxyethyl) terephthalate, bis[4-(2-hydroxyethoxy)phenyl] sulfone, hydroquinone-bis (2-hydroxyethyl)ether, and bis(2-hydroxyethyl) piperazine. Non-limiting examples of suitable diamine are diaminoarenes, and diaminoalkanes. Non-limiting examples of suitable hydroxylamine are p-aminophenol and fluoresceinamine. Non-limiting examples of suitable hydroxythiol are monothiohydroquinone and 4-mercapto-1-butanol. Non-limiting example of suitable thioamine is p-aminobenzenethiol. The intermediate product is isolated and dried. Then, the intermediate product is reacted with malononitrile in the presence of piperidine to form the dimeric electron transport material, which can be purified and dried.

For some other charge transport materials of this invention, the 9-fluorenone-4-carboxylic acid or its derivative react with an alcohol to form the corresponding ester. The ester can then be partially reduced with a reducing agent, such as lithium tri-t-butoxylaluminum hydride, sodium bis (2-methoxyethoxy)aluminum hydride, or diisobutylaluminum hydride, to the corresponding aldehyde without over reduction to alcohol. The aldehyde reacts with a suitable Wittig reagent having two phosphorous ylide groups to form a charge transport material. The Wittig and related reaction is described in Carey et al., "Advanced Organic Chemistry, Part B: Reactions and Synthesis," New York, 1983, pp. 69–77, incorporated herein by reference. The double bond in the resulted charge transport material may also be reduced to a single bond or converted to other functional groups.

Similarly, asymmetric charge transport materials can be formed with or without using an asymmetric linker compound. For example, two differently substituted (9-fluorenylidene)malononitrile groups can be reacted with a symmetric linker compound to form an asymmetric charge transport material. The reaction conditions can be selected to favor the formation of the formation of the asymmetric compound in a sequential or simultaneous reaction. While a mixture of symmetric and asymmetric compounds can be formed, these compounds generally can be separated from each other using available techniques. Alternatively, an asymmetric linker can be used that is more particularly suited to the synthesis of an asymmetric charge transport compound, for example, if each of the reactive functional groups of the linker is only reactive with a functional group of one of the (9-fluorenylidene)malononitrile compounds.

The invention will now be described further by way of the following examples.

EXAMPLES

Example 1

Synthesis And Characterization Charge Transport Materials

This example described the synthesis and chemical characterization of Compounds (2)–(19) in which the numbers refer to formula numbers above. The electronic characterization of materials formed with the compounds are described in the following examples.

Preparation of Compound (2)

A 4.85 g quantity of 9-fluorenone-4-carbonyl chloride (0.02 mole, from Aldrich Chemicals Co, Milwaukee, Wis.) and 100 ml of tetrahydrofuran (from Aldrich) were added to a 250 ml 3-neck round bottom flask equipped with a reflux condenser and a mechanical stirrer. The solution was stirred for approximately ½ hour, and then 1.74 g of 1,10-decanediol (0.01 mole, from Aldrich) in 50 ml of tetrahydrofuran was added, followed by the addition of 2 g of triethylamine (0.02 mole, obtained from Aldrich). The solution was refluxed for 6 hours, filtered hot to remove the triethylamine hydrochloride salt byproduct, and the filtrate was evaporated to remove the volatile compounds and produced a liquid product. After a couple of hours, the liquid product solidified upon standing at room temperature. The crude product was dissolved in hot ethyl acetate, treated with activated charcoal, filtered, and recrystallized by cooling the ethyl acetate solution. The product solids were dried in a 60° C. vacuum oven for 6 hours. A yellow solid (2.5 g, 43% yield) was obtained. The linked di-fluoreneone product had a melting point of 101–102° C. The $^1$H NMR spectrum (300 MHz) of the product in CDCl$_3$ was characterized by the following chemical shifts (δ, ppm) 1.15–1.61 (m, 12H); 1.71–1.92 (q, 4H); 4.34–4.47 (t, 4H); 7.32–7.37 (m, 4H); 7.50 (td, 2H); 7.70 (d, 2H); 7.82 (dd, 2H); 7.93 (dd, 2H); and 8.28 (d, 2H).

To a 250 ml 3-neck round bottom flask equipped with a reflux condenser and a mechanical stirrer were added the linked di-fluoreneone solid (2.4 g, 0.004 mole), methanol (120 ml obtained from Aldrich), and after dissolution, malononitrile (2.64 g, 0.04 mole, obtained from Aldrich) and piperidine (20 drops, obtained from Aldrich). The solution was refluxed for 7 hours. The crude solid product was isolated by filtration and then dissolved in hot ethyl acetate, treated with activated charcoal, filtered, and recrystallized by cooling the ethyl acetate solution. The product solids were dried in a 60° C. vacuum oven for 6 hours. An orange-yellow solid (1.2 g, 45% yield) was obtained. The Compound (2) product had a melting point of 133° C. and a glass transition temperature of 38° C. The $^1$H NMR spectrum (300 MHz) of the product in CDCl$_3$ was characterized by the following chemical shifts (δ, ppm): 1.15–1.53 (m, 12H); 1.73–1.90 (q, 4H); 4.34–4.49 (t, 4H); 7.30–7.42 (m, 4H); 7.45–7.55 (td, 2H); 7.81–7.89 (d, 2H); 8.15–8.23 (dd, 2H); 8.40–8.48 (dd, 2H); and 8.53–8.61 (d, 2H).

Preparation of Compound (3)

A 10.0 g quantity of 9-fluorenone-4-carbonyl chloride (0.04 mole, from Aldrich Chemicals Co, Milwaukee, Wis.) and 100 ml of tetrahydrofuran (from Aldrich) were added to a 250 ml 3-neck round bottom flask equipped with a reflux condenser and a mechanical stirrer. The solution was stirred for approximately ½ hour, then 2.15 g of 1,15-pentanediol (0.02 mole, from Aldrich) in 50 ml of tetrahydrofuran was added followed by the addition of 4.17 g of triethylamine (0.04 mole, from Aldrich). The solution was refluxed for 6 hours and filtered hot to remove triethylamine hydrochloride salt byproduct. The filtrate was evaporated to dryness to obtain the product. The crude linked difluorenone product was dissolved in hot ethyl acetate, treated with activated charcoal, filtered, and recrystallized by cooling the ethyl acetate solution. The product solids were dried in a 60° C. vacuum oven for 6 hours. A yellow solid (6.6 g, 56% yield) was obtained. The product had a melting point of 119–120° C. The $^1$H NMR spectrum (300 MHz) of the product in CDCl$_3$ was characterized by the following chemical shifts (δ, ppm): 1.50–1.77 (m, 2H); 1,82–2.02 (q, 4H); 4.39–4.52 (t, 4H); 7.23–7.41 (m, 4H); 7.45–7.54 (td, 2H); 7.66–7.74 (d, 2H); 7.78–7.85 (dd, 2H); 7.87–7.94 (dd, 2H); and 8.23–8.32 (d, 2H).

A 6.6 g quantity of the linked difluorenone solid (0.0128 mole), 120 ml of methanol (Aldrich), 7.92 g of malononitrile (0.128 mole, from Aldrich), and 20 drops of piperidine (Aldrich) were added to a 250 ml 3-neck round bottom flask equipped with a reflux condenser and a mechanical stirrer. The solution was refluxed for a period of 7 hours. The crude solid product was isolated by filtration and dissolved in hot ethyl acetate, treated with activated charcoal, filtered, and recrystallized by cooling the ethyl acetate solution. The product solids were dried in a 60° C. vacuum oven for 6 hours. An orange-yellow solid (4.5 g, 57% yield) was obtained. The Compound (3) product had a melting point of 163° C. and a glass transition temperature of 71° C. The $^1$H NMR spectrum (300 MHz) of the product in CDCl$_3$ was characterized by the following chemical shifts (δ, ppm): 1.53–1.58 (m, 2H); 1.87–2.01 (q, 4H); 4.41–4.52 (t, 4H); 7.27–7.39 (m, 4H); 7.43–7.53 (td, 2H); 7.79–7.88 (d, 2H); 8.13–8.23 (dd, 2H); 8.40–8.48 (dd, 2H); and 8.54–8.61 (d, 2H).

Preparation of Compound (4)

A 10.0 g quantity of 9-fluorenone-4-carbonyl chloride (0.04 mole, from Aldrich Chemicals Co, Milwaukee, Wis.) and 100 ml of tetrahydrofuran (from Aldrich) were added to a 250 ml 3-neck round bottom flask equipped with a reflux condenser and a mechanical stirrer. The solution was stirred for approximately ½ hour, and then 2.186 g of diethylene glycol (0.02 mole, from Aldrich) in 50 ml of tetrahydrofuran was added, followed by the addition of 4.17 g of triethylamine (0.04 mole, from Aldrich). The solution was refluxed for 6 hours and filtered hot to remove triethylamine hydrochloride salt byproduct. The filtrate was evaporated to dryness to obtain the crude product. The crude product was dissolved in hot ethyl acetate, treated with activated charcoal, filtered, and recrystallized by cooling the ethyl acetate solution. The product solids were dried in a 60° C. vacuum oven for 6 hours. A yellow solid (5.0 g, 47% yield) was obtained. The linked difluorenone product had a melting point of 137° C. The $^1$H NMR spectrum (300 MHz) of the product in CDCl$_3$ was characterized by the following chemical shifts (δ, ppm): 3.88–4.00 (t, 4H); 4.56–4.65 (t, 4H); 7.15–7.34 (m, 4H); 7.40–7.49 (td, 2H); 7.61–7.68 (d, 2H); 7.71–7.77 (dd, 2H); 7.85–7.92 (dd, 2H); and 8.20–8.27 (d, 2H).

A 5.0 g quantity of the linked difluorenone solid (0.01 mole), 120 ml of tetrahydrofuran (Aldrich), 5.94 g of malononitrile (0.09 mole, from Aldrich) and 20 drops of piperidine (Aldrich) were added to a 250 ml 3-neck round bottom flask equipped with a reflux condenser and a mechanical stirrer. The solution was refluxed for a period of 7 hours. The crude solid product was isolated by filtration and dissolved in hot ethyl acetate, treated with activated charcoal, filtered, and recrystallized by cooling the ethyl acetate solution. The product solids were dried in a 60° C. vacuum oven for 6 hours. An orange-yellow solid (3.0 g, 50% yield) was obtained. The Compound (4) product had a melting point of 155° C. and a glass transition temperature of 58° C. The $^1$H NMR spectrum (300 MHz) of the product in CDCl$_3$ was characterized by the following chemical shifts (δ, ppm): 3.89–3.98 (t, 4H); 4.54–4.65 (t, 4H); 7.13–7.24 (m, 4H); 7.35–7.46 (td, 2H); 7.74–7.83 (d, 2H); 8.05–8.17 (dd, 2H); 8.31–8.40 (dd, 2H); and 8.42–8.52 (d, 2H).

Preparation of Compound (5)

A 10.0 g quantity of 9-fluorenone-4-carbonyl chloride (0.04 mole, from Aldrich Chemicals Co, Milwaukee, Wis.) and 100 ml of tetrahydrofuran (from Aldrich) were added to a 250 ml 3-neck round bottom flask equipped with a reflux condenser and a mechanical stirrer. The solution was stirred for approximately ½ hour, and then 3.09 g of triethylene glycol (0.01 mole, obtained from Aldrich) in 50 ml of tetrahydrofuran was added, followed by the addition of 4.17 g of triethylamine (0.04 mole, from Aldrich). The solution was refluxed for 6 hours and filtered hot to remove the triethylamine hydrochloride salt byproduct. The filtrate was evaporated to dryness to obtain the crude product. The crude product was dissolved in hot ethyl acetate, treated with activated charcoal, filtered, and recrystallized by cooling the ethyl acetate solution. The product solids were dried in a 60° C. vacuum oven for 6 hours. A yellow solid (5.8 g, 50 % yield) was obtained. The linked difluorenone product had a melting point of 113–115° C. The ¹H NMR spectrum (300 MHz) of the product in CDCl₃ was characterized by the following chemical shifts (δ, ppm): 3.74–3.76 (t, 3H); 4.46–4.64 (t, 6H); 7.27–7.41 (m, 4H); 7.44–7.57 (td, 2H); 7.65–7.72 (d; 2H); 7.75–7.82 (dd, 2H); 7.91–7.97 (dd, 2H); and 8.21–8.34 (d, 2H).

A 5.8 g quantity of the linked difluorenone yellow solid (0.01 mole), 120 ml of methanol (Aldrich), 6.6 g of malononitrile (0.10 mole, from Aldrich), and 20 drops of piperidine (Aldrich) were added to a 250 ml 3-neck round bottom flask equipped with a reflux condenser and a mechanical stirrer. The solution was refluxed for a period of 7 hours. The crude solid product was isolated by filtration and dissolved in hot toluene, treated with activated charcoal, filtered, and recrystallized by cooling the toluene solution. The product solids were dried in a 60° C. vacuum oven for 6 hours. An orange-yellow solid (2.8 g, 42% yield) was obtained. The product (Compound (5)) had a melting point of 166° C. and a glass transition temperature of 55° C. The ¹H NMR spectrum (300 MHz) of the product in CDCl₃ was characterized by the following chemical shifts (δ, ppm): 3.83–3.92 (t, 6H); 4.48–4.58 (t, 6H); 7.21–7.39 (m, 4H); 7.43–7.53 (td, 2H); 7.81–7.88 (d, 2H); 8.09–8.17 (dd, 2H); 8.33–8.40 (dd, 2H); and 8.41–8.49 (d, 2H).

Preparation of Compound (6)

A 10.0 g quantity of 9-fluorenone-4-carbonyl chloride (0.04 mole, from Aldrich Chemicals Co, Milwaukee, Wis.) and 100 ml of tetrahydrofuran (from Aldrich) were added to a 250 ml 3-neck round bottom flask equipped with a reflux condenser and a mechanical stirrer. The solution was stirred for approximately ½ hour, and then 9.04 g of 4,4'-(9-fluorenylidene) bis (2-phenoxyethanol) (0.02 mole, from Aldrich) in 50 ml of tetrahydrofuran was added, followed by the addition of 4.17 g of triethylamine (0.04 mole, obtained from Aldrich). The solution was refluxed for 6 hours and filtered hot to remove triethylamine hydrochloride salt byproduct. The filtrate was evaporated to dryness to obtain the crude product. The crude product was dissolved in hot tetrahydrofuran, treated with activated charcoal, filtered, and recrystallized by cooling the tetrahydrofuran solution. The product solids were dried in a 60° C. vacuum oven for 6 hours. A yellow solid (9.0 g, 51% yield) was obtained. The linked difluorenone product had a melting point of 137–138° C. A The ¹H NMR spectrum (300 MHz) of the product in CDCl₃ was characterized by the following chemical shifts (δ, ppm): 4.25–4.34 (t, 4H); 4.67–4.77 (t, 4H); 6.71–6.86 (m, 4H); 7.06–7.17 (m, 4H); 7.19–7.48 (m, 12H); 7.65–7.72 (td, 2H); 7.72–7.79 (d, 2H); 7.78–7.84 (dd, 2H); 7.86–7.95 (dd, 2H); and 8.22–8.33 (d, 2H).

A 5.10 g quantity of the yellow solid (0.006 mole), 120 ml of methanol (Aldrich), 3.96 g of malononitrile (0.04 mole, from Aldrich), and 20 drops of piperidine (Aldrich) were added to a 250 ml 3-neck round bottom flask equipped with a reflux condenser and a mechanical stirrer. The solution was refluxed for a period of 7 hours. The crude solid product was isolated by filtration and dissolved in hot ethyl acetate, treated with activated charcoal, filtered, and recrystallized by cooling the ethyl acetate solution. The product solids were dried in a 60° C. vacuum oven for 6 hours. An orange-yellow solid (2.7 g, 47% yield) was obtained. The Compound (6) product had a glass transition temperature of 101° C. The ¹H NMR spectrum (300 MHz) of the product in CDCl₃ was characterized by the following chemical shifts (δ, ppm): 4.20–4.38 (t, 4H); 4.65–4.80 (t, 4H); 6.73–6.86 (m, 4H); 7.07–7.17 (m, 4H); 7.20–7.41 (m, 12H); 7.70–7.80 (td, 2H); 7.85–7.95 (d, 2H); 8.01–8.10 (dd, 2H); 8.20–8.25 (dd, 2H); and 8.35–8.45 (d, 2H)

Preparation of Compound (7)

A 10.0 g quantity of 9-fluorenone-4-carbonyl chloride (0.04 mole, from Aldrich Chemicals Co, Milwaukee, Wis.) and 100 ml of tetrahydrofuran (from Aldrich) were added to a 250 ml 3-neck round bottom flask equipped with a reflux condenser and a mechanical stirrer. The solution was stirred for approximately ½ hour, and then 5.24 g of bis (2-hydroxyethyl) terephthalate (0.02 mole, from Aldrich) in 50 ml of tetrahydrofuran was added, followed by the addition of 4.17 g of triethylamine (0.04 mole, obtained from Aldrich). The solution was refluxed for 6 hours and filtered hot to remove triethylamine hydrochloride salt byproduct. The filtrate was evaporated until dryness to obtain the crude product. The crude product was dissolved in hot ethyl acetate, treated with activated charcoal, filtered, and recrystallized by cooling the ethyl acetate solution. The product solids were dried in a 60° C. vacuum oven for 6 hours. A yellow solid (7.0 g, 52% yield) was obtained. The linked difluorenone product had a melting point of 183–185° C. The ¹H NMR spectrum (300 MHz) of the product in CDCl₃ was characterized by the following chemical shifts (δ, ppm): 4.65–4.87 (t, 8H); 7.27–7.39 (m, 4H); 7.39–7.51 (td, 2H); 7.65–7.74 (d, 2H); 7.80–7.88 (dd, 2H); 7.91–8.00 (dd, 2H); 8.06–8.15 (m, 4H); and 8.24–8.33 (d, 2H).

A 4.6 g quantity of the yellow solid (0.007 mole), 120 ml of methanol (Aldrich), 4.64 g of malononitrile (0.07 mole, from Aldrich), and 20 drops of piperidine (Aldrich) were added to a 250 ml 3-neck round bottom flask equipped with a reflux condenser and a mechanical stirrer. The solution was refluxed for a period of 7 hours. The crude solid product was isolated by filtration and dissolved in a hot tetrahydrofuran/ethyl acetate solvent mixture, treated with activated charcoal, filtered, and recrystallized by cooling the tetrahydrofuran/ethyl acetate solution. The product solids were dried in a vacuum oven at 60° C. for 6 hours. An orange-yellow solid (2.8 g, 52% yield) was obtained. The Compound (7) product had a glass transition temperature of 62° C. The ¹H NMR spectrum (300 MHz) of the product in CDCl₃ was characterized by the following chemical shifts (δ, ppm): 4.63–4.90 (t, 8H); 7.23–7.38 (m, 4H); 7.38–7.50 (td, 2H); 7.65–7.75 (d, 2H); 7.78–7.91 (dd, 2H); 7.92–8.01 (dd, 2H); 8.07–8.16 (m, 4H); and 8.24–8.33 (d, 2H).

Preparation of Compound (8)

A 10.0 g quantity of 9-fluorenone-4-carbonyl chloride (0.04 mole, from Aldrich Chemicals Co, Milwaukee, Wis.) and 100 ml of tetrahydrofuran (from Aldrich) were added to a 250 ml 3-neck round bottom flask equipped with a reflux condenser and a mechanical stirrer. The solution was stirred for approximately ½ hour and then 6.97 g of bis [4-(2-hydroxyethoxy) phenyl] sulfone (0.02 mole, from Aldrich) in 50 ml of tetrahydrofuran was added, followed by the addition of 4.17 g of triethylamine (0.04 mole, obtained from Aldrich). The solution was refluxed for 6 hours and filtered hot to remove triethylamine hydrochloride salt byproduct. The filtrate was evaporated to dryness to obtain the crude product. The crude product was dissolved in a hot tetrahydrofuran, treated with activated charcoal, filtered, and recrystallized by cooling the tetrahydrofuran solution. The product solids were dried in a 60° C. vacuum oven for 6 hours. A yellow solid (9.3 g, 60% yield) was obtained. The ¹H NMR spectrum (300 MHz) of the linked difluorenone product in CDCl₃ was characterized by the following chemical shifts (δ, ppm): 4.35–4.43 (t, 4H); 4.72–4.81 (t, 4H);

6.95–7.05 (m, 4H); 7.27–7.38 (m, 4H); 7.40–7.52 (dd, 2H); 7.66–7.74 (dd, 2H); 7.79–7.94 (m, 8H); and 8.25–8.33 (d, 2H).

A 9.0 g quantity of the yellow solid (0.012 mole), 120 ml of tetrahydrofuran (Aldrich), 7.92 g of malononitrile (0.12 mole, from Aldrich), and 20 drops of piperidine (Aldrich) were added to a 250 ml 3-neck round bottom flask equipped with a reflux condenser and a mechanical stirrer. The solution was refluxed for a period of 7 hours. The crude solid product was isolated by filtration and dissolved in a hot mixture of tetrahydrofuran and methanol, treated with activated charcoal, filtered, and recrystallized by cooling the hot solution. The product solids were dried in a 60° C. vacuum oven for 6 hours. An orange-yellow solid (5.8 g, 57% yield) was obtained. The $^1$H NMR spectrum (300 MHz) of the Compound (8) product in $CDCl_3$ was characterized by the following chemical shifts ($\delta$, ppm): 4.31–4.48 (t, 4H); 4.68–4.86 (t, 4H); 6.94–7.08 (m, 4H); 7.18–7.36 (m, 4H); 7.36–7.51 (dd, 2H); 7.63–7.72 (dd, 2H); 7.82–7.95 (m, 8H); and 8.23–8.32 (d, 2H).

Preparation of Compound (9)

A 10.0 g quantity of 9-fluorenone-4-carbonyl chloride (0.04 mole, from Aldrich Chemicals Co, Milwaukee, Wis.) and 100 ml of tetrahydrofuran (from Aldrich) were added to a 250 ml 3-neck round bottom flask equipped with a reflux condenser and a mechanical stirrer. The solution was stirred for approximately ½ hour, and then 4.08 g of hydroquinone bis(2-hydroxyethyl) ether (0.02 mole, obtained from Aldrich) in 50 ml of THF was added, followed by the addition of 4.17 g of triethylamine (0.04 mole, obtained from Aldrich). The solution was refluxed for 6 hours and filtered hot to remove triethylamine hydrochloride salt byproduct. The filtrate was evaporated to dryness to obtain the crude product. The crude product was dissolved in a hot tetrahydrofuran, treated with activated charcoal, filtered, and recrystallized by cooling the tetrahydrofuran solution. The product solids were dried in a 60° C. vacuum oven for 6 hours. A yellow solid (5.4 g, 43% yield) was obtained. The linked difluorenone product had a melting point of 163–164° C. The $^1$H NMR spectrum (300 MHz) of the product in $CDCl_3$ was characterized by the following chemical shifts ($\delta$, ppm): 4.26–4.38 (t, 4H); 4.70–4.81 (t, 4H); 6.86–6.95 (m, 4H); 7.30–7.40 (m, 4H); 7.41–7.52 (td, 2H); 7.67–7.74 (d, 2H); 7.80–7.87 (dd, 2H); 7.92–8.01 (dd, 2H); and 8.27–8.36 (d, 2H).

A 5.4 g quantity of the yellow, linked difluorenone solid (0.009 mole), 120 ml of methanol (Aldrich), 5.95 g of malononitrile (0.09 mole, from Aldrich), and 20 drops of piperidine (Aldrich) were added to a 250 ml 3-neck round bottom flask equipped with a reflux condenser and a mechanical stirrer. The solution was refluxed for a period of 7 hours. The crude product was isolated by filtration and dissolved in a hot mixture of tetrahydrofuran and methanol solvent, treated with activated charcoal, filtered, and recrystallized by cooling the hot solution. The product solids were dried in a 60° C. vacuum oven for 6 hours. An orange-yellow solid (2.7 g, 42% yield) was obtained. The Compound (9) product had a melting point of 166° C. and a glass transition temperature of 53° C. The $^1$H NMR spectrum (300 MHz) of the product in $CDCl_3$ was characterized by the following chemical shifts ($\delta$, ppm): 4.24–4.42 (t, 4H); 4.68–4.86 (t, 4H); 6.80–6.95 (m, 4H); 7.29–7.40 (m, 4H); 7.40–7.53 (td, 2H); 7.67–7.75 (d, 2H); 7.78–7.91 (dd, 2H); 7.92–8.01 (dd, 2H); and 8.28–8.36 (d, 2H).

Preparation of Compound (10)

A 10.0 g of 9-fluorenone-4-carbonyl chloride (0.04 mole, from Aldrich Chemicals Co, Milwaukee, Wis.) and 100 ml of tetrahydrofuran (from Aldrich) were added to a 250 ml 3-neck round bottom flask equipped with a reflux condenser and a mechanical stirrer. The solution was stirred for approximately ½ hour, and then 3.60 g of bis(2-hydroxyethyl)piperazine (0.02 mole, obtained from Aldrich) in 50 ml of tetrahydrofuran was added, followed by the addition of 4.17 g of triethylamine (0.04 mole, obtained from Aldrich). The solution was refluxed for 6 hours and filtered hot to remove triethylamine hydrochloride salt byproduct. The filtrate was evaporated to dryness to obtain the crude product. The crude product was dissolved in a hot tetrahydrofuran, treated with activated charcoal, filtered, and recrystallized by cooling the tetrahydrofuran solution. The product solids were dried in a 60° C. vacuum oven for 6 hours. A yellow solid (8.5 g, 71% yield) was obtained. The $^1$H NMR spectrum (300 Mhz) of the linked difluorenone product in $CDCl_3$ was characterized by the following chemical shifts ($\delta$, ppm): 2.57–2.75 (t, 8H); 2.77–2.92 (t, 4H); 4.41–4.68 (t, 4H); 7.28–7.41 (m, 4H); 7.46–7.57 (td, 2H); 7.66–7.76 (d, 2H); 7.78–7.87 (dd, 2H); 7.89–7.97 (dd, 2H); and 8.25–8.34 (d, 2H).

A 8.5 g quantity of the yellow, linked difluorenone solid (0.0145 mole), 120 ml of methanol (Aldrich), 9.58 g of malononitrile (0.145 mole, from Aldrich), and 20 drops of piperidine (Aldrich) were added to a 250 ml 3-neck round bottom flask equipped with a reflux condenser and a mechanical stirrer. The solution was refluxed for a period of 7 hours. The crude solid product was isolated by filtration and dissolved in a hot mixture of tetrahydrofuran and methanol, treated with activated charcoal, filtered, and recrystallized by cooling the hot solution. The product solids were dried in a 60° C. vacuum oven for 6 hours. An orange-yellow solid (6.7 g, 70% yield) was obtained. The $^1$H NMR spectrum (300 MHz) of the product (Compound (10)) in $CDCl_3$ was characterized by the following chemical shifts ($\delta$, ppm): 2.54–2.74 (t, 8H); 2.75–2.90 (t, 4H); 4.51–4.62 (t, 4H); 7.30–7.42 (m, 4H); 7.45–7.57 (td, 2H); 7.81–7.90 (d, 2H); 8.15–8.26 (dd, 2H); 8.39–8.49 (dd, 2H); and 8.53–8.63 (d, 2H).

Preparation of Compound (11)

A 10.0 g quantity of 9-fluorenone-4-carbonyl chloride (0.04 mole, from Aldrich Chemicals Co, Milwaukee, Wis.) and 100 ml of tetrahydrofuran (from Aldrich) were added to a 250 ml 3-neck round bottom flask equipped with a reflux condenser and a mechanical stirrer. The solution was stirred for approximately ½ hour, and then 5.16 g of 4,4'-thiobisbenzenethiol (0.02 mol, obtained from Aldrich) in 50 ml of tetrahydrofuran was added, followed by the addition of 4.17 g of triethylamine (0.04 mole, obtained from Aldrich). The solution was refluxed for 6 hours and filtered hot to remove triethylamine hydrochloride salt byproduct. The filtrate was evaporated to dryness to obtain the crude product. The crude product was dissolved in a hot mixture of tetrahydrofuran and methanol, treated with activated charcoal, filtered, and recrystallized by cooling the hot solution. The product solids were dried in a 60° C. vacuum oven for 6 hours. A yellow, linked difluorenone solid (6.85 g, 50 % yield) was obtained.

A 6.85 g quantity of the yellow, linked difluorenone solid (0.01 mole), 120 ml of methanol (Aldrich), 6.6 g of malononitrile (0.1 mole, from Aldrich), and 20 drops of piperidine (Aldrich) were added to a 250 ml 3-neck round bottom flask equipped with a reflux condenser and a mechanical stirrer. The solution was refluxed for a period of 7 hours. The crude solid product was isolated by filtration and dissolved in a hot mixture of tetrahydrofuran and methanol, treated with activated charcoal, filtered, and recrystallized by cooling the hot solution. The product solids were dried in a 60° C. vacuum oven for 6 hours. An orange-yellow, Compound (11) solid (4.58 g, 60% yield) was obtained.

Preparation of Compound (12)

Compound (12) can be prepared by a similar method to the preparation of Compound (11) except 1,4-benzenedithiol (available from ABCR GmbH & Co. KG, Karlsruhe, Germany) replaces 4, 4'-thiobisbenzenethiol.

Preparation of Compound (13)

Compound (13) can be by a similar method to the preparation of Compound (11) except 1,3-benzenedithiol (obtained from Aldrich) replaces 4,4'-thiobisbenzenethiol.

Preparation of Compound (14)

Compound (14) can be prepared by a similar method to the preparation of Compound (11) except bis(4,4'-thiolphenyl)sulfone (which can be prepared according to the reference of Alov E. M., Nikiforov S. E., Novikov S. E., Kobylinskii D. B., Moskvichev Y. A., Kryukova G. G., Yasinskii O. A., Budanov N. A., "Synthesis and acid-base properties of thiols and sulfinic acids on diphenyl bridged compound series," *Zhurnal Organicheskoi Khimii*, 34 (8), 1998, p. 1214–1218, incorporated herein by reference) replaces 4,4'-thiobisbenzenethiol.

Preparation of Compound (15)

Compound (15) can be by a similar method to the preparation of Compound (11) except 2,5-dimecapto-1,3,4-thiadiazole (from Aldrich, Milwaukee, Wis.) replaces 4,4'-thiobisbenzenethiol.

Preparation of Compound (16)

Compound (16) can be prepared by a similar method to the preparation of Compound (11) except 1,4-dihydroxybenzene (from Aldrich) replaces 4,4'-thiobisbenzenethiol.

Preparation of Compound (17)

Compound (17) can be prepared by a similar method to the preparation of Compound (11) except 1,3-dihydroxybenzene (from Aldrich) replaces 4,4'-thiobisbenzenethiol.

Preparation of Compound (18)

Compound (18) can be prepared by a similar method to the preparation of Compound (11) except 4,4'-sulfonyldiphenol (from Aldrich) replaces 4,4'-thiobisbenzenethiol.

Preparation of Compound (19)

A 10.0 g quantity of 9-fluorenone-4-carbonyl chloride (0.041 mol, from Aldrich Chemicals Co, Milwaukee, Wis. 53201, USA) and 100 ml of absolute dioxane (from Aldrich) were added to a 250 ml 3-neck round bottom flask equipped with a reflux condenser and a mechanical stirrer. The solution was stirred for approximately ½ hour, and then 3.8 g of 1,9-nonanedithiol (0.020 mol, obtained from Aldrich) was added, followed by the addition of 5.8 ml of triethylamine (0.042 mole, obtained from Aldrich). The solution was intensively stirred at 80° C. for 2 hours under argon. The reaction mixture was filtered hot to remove triethylamine hydrochloride salt by-product, and the filtrate was concentrated to 35–40 ml by evaporation. The obtained solution was diluted with 50 ml of methanol. The crystals that formed upon standing were filtered off and washed with cold methanol to give 9.6 g (81 % yield) of an intermediate product.

A 6.7 g quantity of the intermediate product (0.01 mol, prepared in previous step), 80 ml of absolute dioxane (Aldrich), 6.0 g of malononitrile (0.1 mol, from Aldrich), and 20 drops of piperidine (Aldrich) were added to a 250 ml 3-neck round bottom flask equipped with a reflux condenser and a mechanical stirrer. The solution was intensively stirred at 80° C. for 5 hours under argon and then evaporated to dryness. Next, 80 ml of methanol was added to the residue, the mixture was refluxed for 1 h, and then intensively stirred at room temperature for 5 h. The crystals that formed were filtered off and washed with cold methanol to give 3 g (39 % yield) of Compound (19). The product had a melting point of 76–78° C. (recrystallized from dioxane/methanol, 1/1 v/v). A mass spectra (APCI$^+$) fraction with a molecular weight of 701 (M+H)$_+$ was observed. The $^1$H NMR spectrum (250 MHz) of the product in CDCl$_3$ was characterized by the following chemical shifts (δ, ppm): 8.6–8.3 (m, 6H, Ar); 7.65 (d, 2H, Ar); 7.55–7.15 (m, 6H, CH$_3$Ph); 3.2 (t, 4H, CH$_2$S); and 2.0–1.3 (m, 14H, SCH$_2$(CH$_2$)$_7$CH$_2$S). The IR spectrum of the product was characterized by the following absorption peaks (v in cm$^{-1}$): 2225 (CN), 1667 (COS). An elemental analysis yielded the following results in weight percent: C, 73.66; H, 4.51; and N, 7.74; which compared with calculated values for C$_{43}$H$_{32}$N$_4$O$_2$S$_2$ in weight percent of C, 73.69; H, 4.60; and N, 7.99.

Preparation of (4-n-Butoxycarbonyl-9-fluorenylidene)malononitrile

A 460 g quantity of concentrated sulfuric acid (4.7 moles, analytical grade, from Sigma-Aldrich, Milwaukee, Wis.) and 100 g of diphenic acid (0.41 mole, from Acros Fisher Scientific Company Inc., Hanover Park, Ill.) were added to a 1-liter 3-neck round bottom flask, equipped with a thermometer, mechanical stirrer and reflux condenser. Using a heating mantle, the flask was heated to 135–145° C. for 12 minutes. After cooling to room temperature, the solution was added to a 4-liter Erlenmeyer flask containing 3 liter of water. The mixture was stirred mechanically and brought to a gentle boil for one hour. The yellow solid that formed was filtered out hot, washed with hot water until the pH of the washing water was neutral, and dried overnight in the fume-hood. The yellow solid was fluorenone-4-carboxylic acid (75 g, 80% yield). The product had a melting point of 223–224° C. The $^1$H NMR spectrum (300 MHz) of the product in CDCl$_3$ was characterized by the following chemical shifts (δ, ppm): 7.39–7.50 (m, 2H); 7.79–7.70 (q, 2H); 7.74–7.85 (d, 1H); 7.88–8.00 (d, 1H); and 8.18–8.30 (d, 1H), where d is doublet, t is triplet, m is multiplet; dd is double doublet, q is quintet.

A 70 g quantity (0.312 mole) of fluorenone-4-carboxylic acid, 480 g (6.5 mole) of n-butanol (from Fisher Scientific Company Inc., Hanover Park, Ill.), 1000 ml of toluene, and 4 ml of concentrated sulfuric acid were added to a 2-liter round bottom flask equipped with a mechanical stirrer and a reflux condenser with a Dean Stark apparatus. The solution was refluxed for 5 hours with aggressive agitation and refluxing, during which time approximately 6 g of water were collected in the Dean Stark apparatus. The flask was cooled to room temperature. The solvents were evaporated and the residue was added with agitation to 4-liter of 3% sodium bicarbonate aqueous solution. The solid was filtered off, washed with water until the pH of the water was neutral, and dried in the hood overnight. The product was n-butyl fluorenone-4-carboxylate ester (70 g, 80% yield). The $^1$H NMR spectrum (300 MHz) of the product in CDCl$_3$ was characterized by the following chemical shifts (δ, ppm): 0.87–1.09 (t, 3H); 1.42–1.70 (m, 2H); 1.75–1.88 (q, 2H); 4.26–4.64 (t, 2H); 7.29–7.45 (m, 2H); 7.46–7.58 (m, 1H); 7.60–7.68 (dd, 1H); 7.75–7.82 (dd, 1H); 7.90–8.00 (dd, 1H); and 8.25–8.35 (dd, 1H).

A 70 g quantity (0.25 mole) of n-butyl fluorenone-4-carboxylate ester, 750 ml of absolute methanol, 37 g (0.55 mole) of malononitrile (from Sigma-Aldrich, Milwaukee, Wis.), and 20 drops of piperidine (from Sigma-Aldrich, Milwaukee, Wis.) were added to a 2-liter, 3-neck round bottom flask equipped with a mechanical stirrer and a reflux condenser. The solution was refluxed for 8 hours, and then the flask was cooled to room temperature. The orange crude solid product was filtered, washed twice with 70 ml of methanol and once with 150 ml of water, and dried overnight in the fume-hood. The crude orange product was dissolved in a hot mixture of acetone and methanol in 2:1 ratio by volume, treated with activated charcoal, filtered, and recrystallized by cooling the solution to 0° C. for 16 hours. The crystals were filtered and dried in a vacuum oven at 50° C. for 6 hours to obtain 60 g of purified (4-n-butoxycarbonyl-9-fluorenylidene) malononitrile. The product had a melting point of 99–100° C. The $^1$H NMR spectrum (300 MHz) of the product in $CDCl_3$ was characterized by the following chemical shifts ($\delta$, ppm): 0.74–1.16 (t, 3H); 1.38–1.72 (m, 2H); 1.70–1.90 (q, 2H); 4.29–4.55 (t, 2H); 7.31–7.43 (m, 2H); 7.45–7.58 (m, 1H); 7.81–7.91 (dd, 1H); 8.15–8.25 (dd, 1H); 8.42–8.52 (dd, 1H); and 8.56–8.66 (dd, 1H).

Example 2

Formation of Organophotoreceptor Samples

This example describes the formation of 4 samples and one comparative sample using the compounds described in Example 1.

Sample 1

Sample 1 was a single layer organophotoreceptor coated on a 30 mm diameter anodized aluminum drum substrate. The coating solution for the single layer organophotoreceptor was prepared by combining 1.51 g of MPCT-10 (a charge transfer material, commercially obtained from Mitsubishi Paper Mills, Tokyo, Japan) dissolved in 6.03 g of tetrahydrofuran and 0.44 g of Compound (2) dissolved in 1.74 g of tetrahydrofuran and shaken until the components were thoroughly mixed. A 6.4 g quantity of a 13 wt % polyvinyl butyral resin (BX-5, commercially obtained from Sekisui Chemical Co. Ltd., Japan) in tetrahydrofuran pre-mix solution, 3.20 g of tetrahydrofuran, and 0.68 g of a CGM mill-base containing 18.4 wt % of titanyl oxyphthalocyanine plus polyvinyl butyral resin at a ratio of 2.3:1 (BX-5, commercially obtained from Sekisui Chemical Co. Ltd., Japan) in tetrahydrofuran was added to this mixture.

The CGM mill-base was obtained by milling 112.7 g of titanyl oxyphthalocyanine (from H. W. Sands Corp., Jupiter, Fla.) with 49 g of the polyvinyl butyral resin (BX-5) in 651 g of methylethylketone on a horizontal sand mill (model LMC12 DCMS, from Netzsch Incorporated, Exton, Pa) with 1-micron zirconium beads using recycle mode for 4 hours.

After mixing the solution on a mechanical shaker for approximately 1 hour, the single layer coating solution was ring coated onto the 30 mm diameter anodized aluminum drum at a rate of 112 mm/min, which was followed by drying the coating drum in an oven at 110° C. for 5–10 minutes. The dry photoconductor film thickness was 11 um±0.5 um.

Sample 2

Sample 2 was a single layer organophotoreceptor coated on a 30 mm diameter anodized aluminum drum substrate. The coating solution for the single layer organophotoreceptor was prepared by combining 1.51 g of MPCT-10 (a charge transfer material, from Mitsubishi Paper Mills, Tokyo, Japan) dissolved in 6.03 g of tetrahydrofuran and 0.44 g of Compound (6) dissolved in 1.74 g of tetrahydrofuran and shaken until the components were thoroughly mixed. A 6.4 g quantity of a 13 wt % polyvinyl butyral resin (BX-5, from Sekisui Chemical Co. Ltd., Japan) in tetrahydrofuran pre-mix solution, 3.20 g of tetrahydrofuran, and 0.68 g of a CGM mill-base containing 18.4 wt % of titanyl oxyphthalocyanine plus polyvinyl butyral resin at a ratio of 2.3:1 (BX-5, from Sekisui Chemical Co. Ltd., Japan) in tetrahydrofuran was added to this mixture.

The CGM mill-base was obtained by milling 112.7 g of titanyl oxyphthalocyanine (from H. W. Sands Corp., Jupiter, Fla.) with 49 g of the polyvinyl butyral resin (BX-5) in 651 g of methylethylketone on a horizontal sand mill (model LMC12 DCMS, from Netzsch Incorporated, Exton, Pa.) with 1-micron zirconium beads using recycle mode for 4 hours.

After mixing the solution on a mechanical shaker for approximately 1 hour, the single layer coating solution was ring coated onto the 30 mm diameter anodized aluminum drum at a rate of 112 mm/min, which was followed by drying the coating drum in an oven at 110° C. for 5–10 minutes. The dry photoconductor film thickness was 11 um±0.5 um.

Sample 3

Sample 3 was a single layer organophotoreceptor coated on a 30 mm diameter anodized aluminum drum substrate. The coating solution for the single layer organophotoreceptor was prepared by combining 1.51 g of MPCT-10 (a charge transfer material, from Mitsubishi Paper Mills, Tokyo, Japan) dissolved in 6.03 g of tetrahydrofuran and 0.44 g of Compound (8) dissolved in 1.74 g of tetrahydrofuran and shaken until the components were thoroughly mixed. A 6.4 g quantity of a 13 wt % polyvinyl butyral resin (BX-5, from Sekisui Chemical Co. Ltd., Japan) in tetrahydrofuran pre-mix solution, 3.20 g of tetrahydrofuran, and 0.68 g of a CGM mill-base containing 18.4 wt % of titanyl oxyphthalocyanine plus polyvinyl butyral resin at a ratio of 2.3:1 (BX-5, from Sekisui Chemical Co. Ltd., Japan) in tetrahydrofuran was added to this mixture.

The CGM mill-base was obtained by milling 112.7 g of titanyl oxyphthalocyanine (from H. W. Sands Corp., Jupiter, Fla.) with 49 g of the polyvinyl butyral resin (BX-5) in 651 g of methylethylketone on a horizontal sand mill (model LMC12 DCMS, from Netzsch Incorporated, Exton, Pa.) with 1-micron zirconium beads using recycle mode for 4 hours.

After mixing the solution on a mechanical shaker for approximately 1 hour, the single layer coating solution was ring coated onto the 30 mm diameter anodized aluminum drum at a rate of 112 mm/min, which was followed by drying the coated drum in an oven at 110° C. for 5–10 minutes. The dry photoconductor film thickness was 11 um±0.5 um.

Sample 4

Sample 4 was a single layer organophotoreceptor coated on a 30 mm diameter anodized aluminum drum substrate. The coating solution for the single layer organophotoreceptor was prepared by combining 1.51 g of MPCT-10 (a charge transfer material, from Mitsubishi Paper Mills, Tokyo, Japan) dissolved in 6.03 g of tetrahydrofuran and 0.44 g of Compound (5) dissolved in 1.74 g of tetrahydrofuran and shaken until the components were thoroughly mixed. A 6.4 g quantity of a 13 wt % polyvinyl butyral resin (BX-5, from Sekisui Chemical Co. Ltd., Japan) in tetrahydrofuran pre-mix solution, 3.20 g of tetrahydrofuran, and 0.68 g of a CGM mill-base containing 18.4 wt % of titanyl oxyphthalocyanine plus polyvinyl butyral resin at a ratio of 2.3:1 (BX-5, from Sekisui Chemical Co. Ltd., Japan) in tetrahydrofuran was added to this mixture.

The CGM mill-base was obtained by milling 112.7 g of titanyl oxyphthalocyanine (from H. W. Sands Corp., Jupiter, Fla.) with 49 g of the polyvinyl butyral resin (BX-5) in 651 g of methylethylketone on a horizontal sand mill (model LMC12 DCMS, from Netzsch Incorporated, Exton, Pa.) with 1-micron zirconium beads using recycle mode for 4 hours.

After mixing the solution on a mechanical shaker for approximately 1 hour, the single layer coating solution was ring coated onto the 30 mm diameter anodized aluminum drum at a rate of 112 mm/min, which was followed by drying the coated drum in an oven at 110° C. for 5–10 minutes. The dry photoconductor film thickness was 11 um±0.5 um.

Comparative Sample A

Comparative Example A was a single layer organophotoreceptor coated on a 30 mm diameter anodized aluminum drum substrate. The coating solution for the single layer organophotoreceptor was prepared by combining 1.51 g of MPCT-10 (a charge transfer material, from Mitsubishi Paper Mills, Tokyo, Japan) dissolved in 6.03 g of tetrahydrofuran and 0.44 g of (4-n-butoxycarbonyl-9-fluorenylidene)malononitrile dissolved in 1.74 g of tetrahydrofuran and shaken until the components were thoroughly mixed. A 6.4 g of a 13 wt % polyvinyl butyral resin (BX-5, from Sekisui Chemical Co. Ltd., Japan) in tetrahydrofuran pre-mix solution, 3.20 g of tetrahydrofuran, and 0.68 g of a CGM mill-base containing 18.4 wt % of titanyl oxyphthalocyanine plus polyvinyl butyral resin at a ratio of 2.3:1 (BX-5, from Sekisui Chemical Co. Ltd., Japan) in tetrahydrofuran was added to this mixture.

The CGM mill-base was obtained by milling 112.7 g of titanyl oxyphthalocyanine (from H. W. Sands Corp., Jupiter, Fla.) with 49 g of the polyvinyl butyral resin (BX-5) in 651 g of methylethylketone on a horizontal sand mill (model LMC12 DCMS, from Netzsch Incorporated, Exton, Pa.) with 1-micron zirconium beads using recycle mode for 4 hours.

After mixing the solution on a mechanical shaker for approximately 1 hour, the single layer coating solution was ring coated onto the 30 mm diameter anodized aluminum drum at a rate of 112 mm/min, which was followed by drying the coated drum in an oven at 110° C. for 5–10 minutes. The dry photoconductor film thickness was 11 um±0.5 um.

Example 3

Electrostatic Testing

Extended electrostatic cycling performance of the charge transport materials was determined using an in-house designed and developed test bed. Electrostatic evaluation on the 30 mm drum test bed is designed to accelerate electrostatic fatigue during extended cycling by increasing the charge-discharge cycling frequency and decreasing the recovery time as compared to larger diameter drum test beds with longer process speeds. The location of each station in the tester (distance and elapsed time per cycle) is given as follows.

| Electrostatic test stations around the 30 mm drum at 12.7 cm/s. | | | |
|---|---|---|---|
| Station | Degrees | Total Distance, cm | Total Time, sec |
| Erase Bar Center | 0° | Initial, 0 cm | Initial, 0 s |
| Corotron Charger | 87.3° | 2.29 | 0.18 |
| Laser Strike | 147.7° | 3.87 | 0.305 |
| Probe #1 | 173.2° | 4.53 | 0.36 |
| Probe #2 | 245.9° | 6.44 | 0.51 |
| Erase Bar Center | 360° | 9.425 | 0.74 |

The erase bar is an array of laser emitting diodes (LED) with a wavelength of 720 nm that discharges the surface of the organophotoreceptor. The scorotron charger comprises a wire that permits the transfer of a desired amount of charge to the surface of the organophotoreceptor.

From the table, the first electrostatic probe (Trek™ 344 electrostatic meter) is located 0.055 s after the laser strike station and 0.18 s after the corotron charger. In addition, the second probe (Trek™ 344 electrostatic meter) is located 0.15 s from the first probe and 0.33 s from the corotron charger. All measurements were performed at 20° C. and 30% relative humidity.

Electrostatic measurements were obtained as a compilation of several tests. The first three diagnostic tests (prodtest initial, VlogE initial, dark decay initial) are designed to evaluate the electrostatic cycling of a new, fresh sample and the last three, identical diagnostic tests (prodtest final, VlogE final, dark decay final) are run after cycling of the sample (longrun). The laser is operated at 780 nm, 600 dpi, 50 um spot size, 60 nanoseconds/pixel expose time, 1,800 lines per second scan speed, and a 100% duty cycle. The duty cycle is the percent exposure of the pixel clock period, i.e., the laser is on for the full 60 nanoseconds per pixel at a 100% duty cycle.

Electrostatic Test Suite

1. PRODTEST: Charge acceptance ($V_{acc}$) and discharge voltage ($V_{dis}$) were established by subjecting the samples to corona charging (erase bar always on) for three complete drum revolutions (laser off); discharged with the laser @ 780 nm & 600 dpi on the forth revolution; completely charged for the next three revolutions (laser off); discharged with only the erase lamp @ 720 nm on the eighth revolution (corona and laser off) to obtain residual voltage ($V_{res}$); and, finally, completely charged for the last three revolutions (laser off). The contrast voltage ($V_{con}$) is the difference between $V_{acc}$ and $V_{dis}$ and the functional dark decay ($V_{dd}$) is the difference in charge acceptance potential measured by probes #1 and #2.
2. VLOGE: This test measures the photoinduced discharge of the photoconductor to various laser intensity levels by monitoring the discharge voltage of the sample as a function of the laser power (exposure duration of 50 ns) with fixed exposure times and constant initial potentials. The functional photosensitivity, $S_{780\,nm}$, was determined from this diagnostic test.
3. DARK DECAY: This test measures the loss of charge acceptance with time without laser or erase illumination for 90 seconds and can be used as an indicator of i) the injection of residual holes from the charge generation layer to the charge transport layer, ii) the thermal liberation of trapped charges, and iii) the injection of charge from the surface or aluminum ground plane.

4. LONGRUN: The sample was electrostatically cycled for 100,500 or 4,000 drum revolutions according to the following sequence per each drum revolution. The sample was charged by the corona, the laser was cycled on and off (80–100° sections) to discharge a portion of the drum and, finally, the erase lamp discharged the whole drum in preparation for the next cycle. The laser was cycled so that the first section of the drum was never exposed, the second section was always exposed, the third section was never exposed, and the final section was always exposed. This pattern was repeated for a total of 100,500 or 4,000 drum revolutions, and the data for every $5^{th}$ cycle, $25^{th}$ cycle or $200^{th}$ cycle was recorded.

5. After the LONGRUN test, the PRODTEST, VLOGE, DARK DECAY diagnostic tests were run again.

polyester film with conductive Al layer by the dip roller method. After drying for 1 h at 80° C., a clear 10 μm thick layer was formed.

Sample 6

A mixture of 0.1 g of the Compound (19) and 0.1 g of polycarbonate (IupilonZ-200™ from Mitsubishi Gas Chemical Co.) was dissolved in 2 ml of tetrahydrofuran. The solution was coated on the polyester film with conductive Al layer by the dip roller method. After drying for 1 hour at 80° C., a clear 10 μm thick layer was formed.

Comparative Sample B

A mixture of 0.1 g of (4-n-butoxycarbonyl-9-fluorenylidene) malononitrile) and 0.1 g of polycarbonate (IupilonZ-200™, from Mitsubishi Gas Chemical Co.) was dissolved in 2 ml of tetrahydrofuran. The solution was coated on the polyester film with conductive Al layer by the dip roller method. After drying for 1 h at 80° C., a clear 10 μm thick layer was formed.

TABLE 1

Electrostatic Test Results before and after 100, 500, and 4000 cycles.

| Sample | Prodtest Initial | | | | | | Prodtest Final | | | | |
|---|---|---|---|---|---|---|---|---|---|---|---|
| | $V_{acc}$ | $V_{dis}$ | $V_{con}$ | $S_{780nm}$ | $V_{dd}$ | $V_{res}$ | $V_{acc}$ | $V_{dis}$ | $V_{con}$ | $V_{dd}$ | $V_{res}$ |
| 100 cycles | | | | | | | | | | | |
| 1 | 599 | 114 | 485 | 251 | 62 | 62 | 589 | 102 | 487 | 67 | 29 |
| Comparative Sample A | 601 | 40 | 561 | 419 | 51 | 51 | 586 | 39 | 547 | 39 | 9 |
| 500 cycles | | | | | | | | | | | |
| 1 | 999 | 91 | 908 | 236 | 22 | 27 | 799 | 90 | 709 | 26 | 33 |
| 2 | 932 | 95 | 837 | 251 | 20 | 42 | 780 | 99 | 681 | 11 | 44 |
| 3 | 1035 | 91 | 944 | 251 | 45 | 36 | 784 | 85 | 699 | 57 | 40 |
| 4 | 518 | 28 | 490 | 377 | 57 | 19 | 446 | 32 | 414 | 62 | 12 |
| Comparative Sample A | 905 | 61 | 844 | 419 | 29 | 21 | 618 | 58 | 560 | 60 | 22 |
| 4000 cyles | | | | | | | | | | | |
| 1 | 627 | 103 | 524 | 290 | 59 | 30 | 433 | 88 | 345 | 79 | 28 |
| Comparative Sample A | 609 | 40 | 569 | 419 | 52 | 9 | 429 | 44 | 385 | 65 | 14 |

Note:
Fresh samples were used for each evaluation.

In the above tables, the radiation sensitivity ($S_{780\ nm}$ Sensitivity at 780 nm in m2/J) of the xergraphic process was determined from the information obtained during the VLOGE deagnostic run by calculating the reciprocal of the product of the laser power required to discharge the photoreceptor to ½ of its initial potential, the exposure duration, and 1/spot size.

Example 3

Charge Mobility Measurements

This example describes the measurement of charge mobility for charge transport materials such as Compound (2) and Compound (19) above.

Sample 5

A mixture of 0.1 g of the Compound (2) and 0.1 g of polyvinylbutyral (S-LEC B BX-1, from Sekisui) was dissolved in 2 ml of THF. The solution was coated on the Mobility Measurements Each sample was corona charged positively up to a surface potential U and illuminated with 2 ns long nitrogen laser light pulse. The electron mobility μ was determined as described in Kalade et al., "Investigation of charge carrier transfer in electrophotographic layers of chalkogenide glasses," Proceeding IPCS 1994: The Physics and Chemistry of Imaging Systems, Rochester, N.Y., pp. 747–752, incorporated herein by reference. The electron mobility measurement was repeated with changes to the charging regime to charge the sample to different U values, which correspond to different electric field strengths inside the layer E. This dependence on electric field strength was approximated by the formula $$\mu=\mu_0 e^{\alpha\sqrt{E}}.$$

Here E is electric field strength, $\mu_0$ is the zero field mobility and α is Pool-Frenkel parameter. The mobility characterizing parameters $\mu_0$ and α values as well as the mobility value at the $6.4\times10^5$ V/cm field strength as determined from these measurements are given in Table 2.

TABLE 2

| Sample | $\mu_0$ (cm$^2$/V·s) | $\mu$ (cm$^2$/V·s) at 6.4·10$^5$ V/cm | $\alpha$ (cm/V)$^{0.5}$ |
|---|---|---|---|
| 5 | 2·10$^{-11}$ | 7·10$^{-10}$ | 0.005 |
| 6 | 3.8·10$^{-9}$ | 3.8·10$^{-7}$ | 0.0058 |
| Comparative Sample B | 1.7·10$^{-8}$ | 2.4·10$^{-6}$ | 0.0062 |

As understood by those skilled in the art, additional substitution, variation among substituents, and alternative methods of synthesis and use may be practiced within the scope and intent of the present disclosure of the invention. The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. An organophotoreceptor comprising an electrically conductive substrate and a photoconductive element on the electrically conductive substrate, the photoconductive element comprising:

(a) a charge transport material having the formula

X-Z-X' where X and X', each independently, have the formula

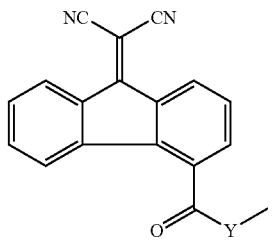

where Y is O—CH$_2$—CH$_2$—O, S, or NR$_8$ and R$_8$ is H, an alkyl group, an alkenyl group, an aromatic group, or a heterocyclic group, and Z is a linking group having the formula —(CH$_2$)$_m$—, branched or linear, where m is an integer between 1 and 30, inclusive, and one or more of the methylene groups may be replaced by O, S, C=O, Si=O, S(=O)$_2$, P(=O)$_2$, an aromatic group, a heterocyclic group, an aliphatic cyclic group, a Si(R$_1$)(R$_2$) group, a BR$_3$ group, a NR$_4$ group, a CHR$_5$ group, or a CR$_6$R$_7$ group where R$_1$, R$_2$, R$_3$, R$_4$, R$_5$, R$_6$, and R$_7$ are, each independently, H, halogen, hydroxyl, thiol, an alkoxy group, an alkyl group, an alkenyl group, an aromatic group, a heterocyclic group, or a part of a cyclic ring; and (b) a charge generating compound.

2. An organophotoreceptor according to claim 1 wherein Z comprises an aromatic group or a heterocyclic group.

3. An organophotoreceptor according to claim 1 wherein the charge transport material has a formula selected form the group consisting of the following:

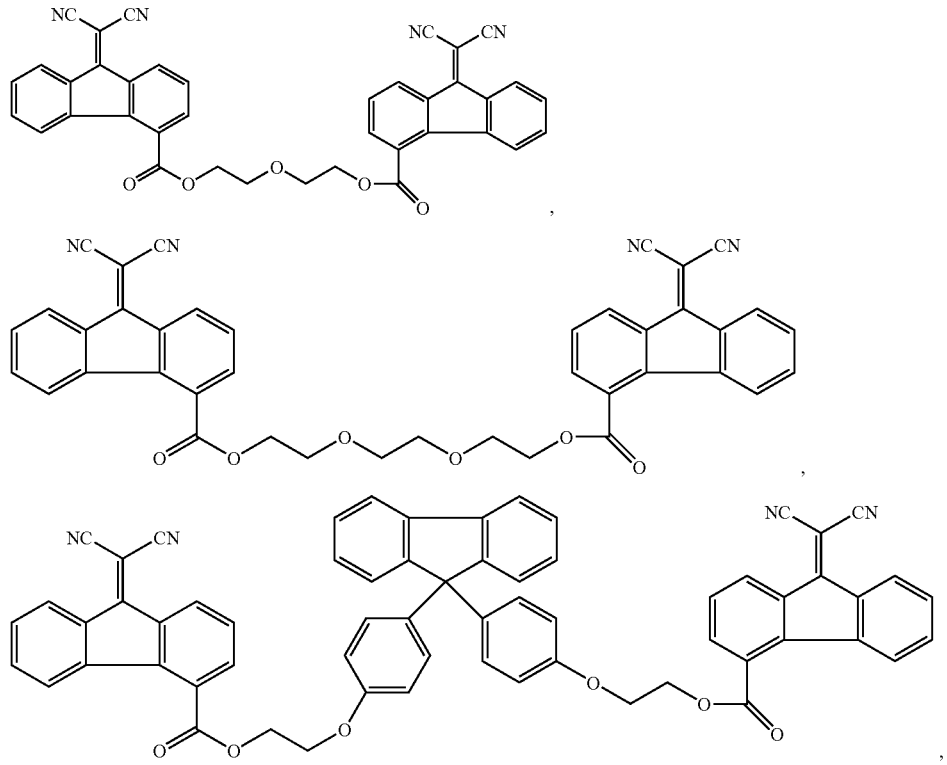

-continued
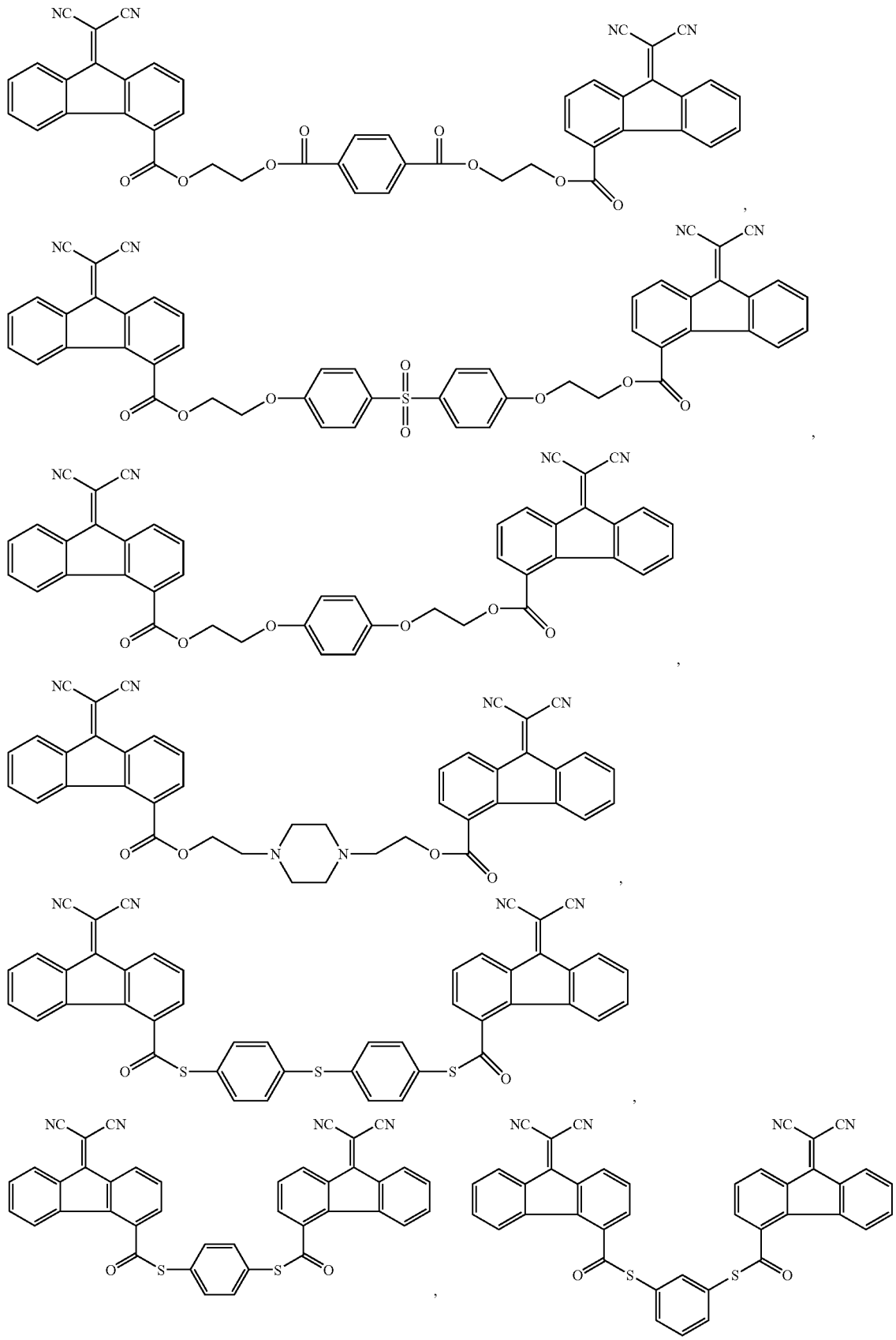

-continued

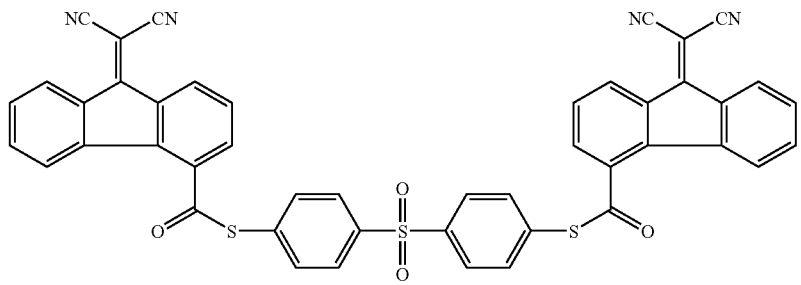

,

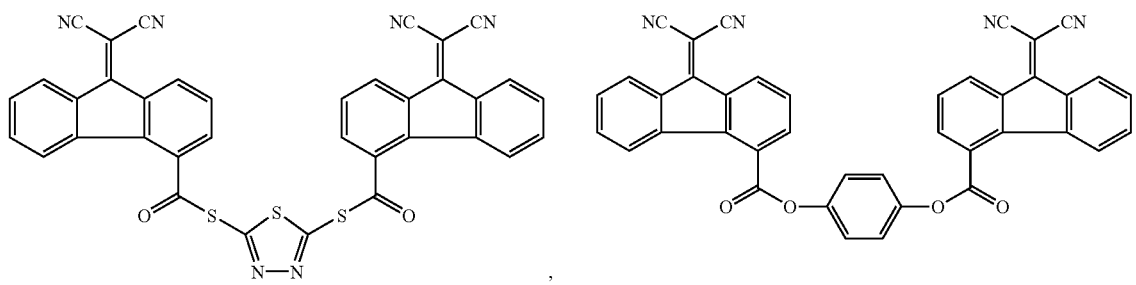

,

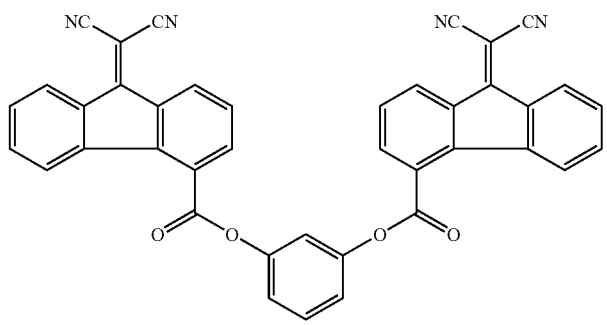

, and

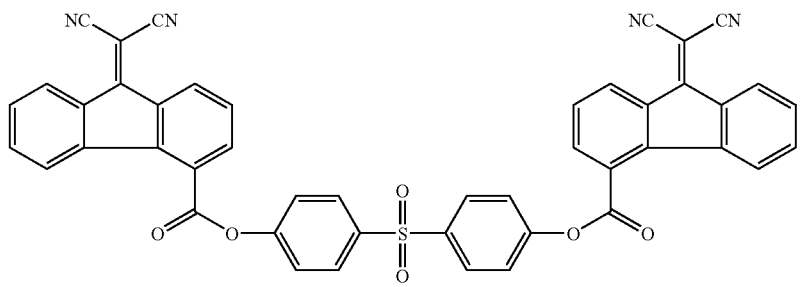

.

4. An organophotoreceptor according to claim 1 wherein the photoconductive element further comprises a second charge transport material.

5. An organophotoreceptor according to claim 4 wherein the second charge transport material comprises a charge transport compound.

6. An organophotoreceptor according to claim 1 wherein the photoconductive element further comprises a binder.

7. An electrophotographic imaging apparatus comprising:
(a) a light imaging component; and
(b) an organophotoreceptor oriented to receive light from the light imaging component, the organophotoreceptor comprising an electrically conductive substrate and a photoconductive element on the electrically conductive substrate, the photoconductive element comprising:
(i) a charge transport material having the formula

X-Z-X' where X and X', each independently, have the formula

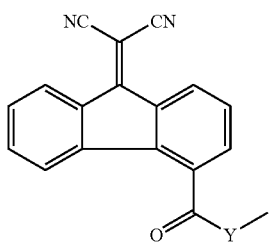

where Y is O—CH$_2$—CH$_2$—O, S, or NR$_8$ and R$_8$ is H, an alkyl group, an alkenyl group, an aromatic group, or a heterocyclic group, and Z is a linking group having the formula —(CH$_2$)$_m$—, branched or linear, where m is an integer between 1 and 30, inclusive, and one or more of the methylene groups may be replaced by O, S, C=O, Si=O, S(=O)$_2$, P(=O)$_2$, an aromatic group, a heterocyclic group, an aliphatic cyclic group, a Si(R$_1$)(R$_2$) group, a BR$_3$ group, a NR$_4$ group, a CHR$_5$ group, or a CR$_6$R$_7$ group where R$_1$, R$_2$, R$_3$, R$_4$, R$_5$, R$_6$, and R$_7$ are, each independently, H, halogen, hydroxyl, thiol, an alkoxy group, an alkyl group, an alkenyl group, an aromatic group, a heterocyclic group, or a part of a cyclic ring; and (ii) a charge generating compound.

8. An electrophotographic imaging apparatus according to claim 7 wherein Z comprises an aromatic group or a heterocyclic group.

9. An electrophotographic imaging apparatus according to claim 7, wherein the charge transport material has a formula selected form the group consisting of the following:

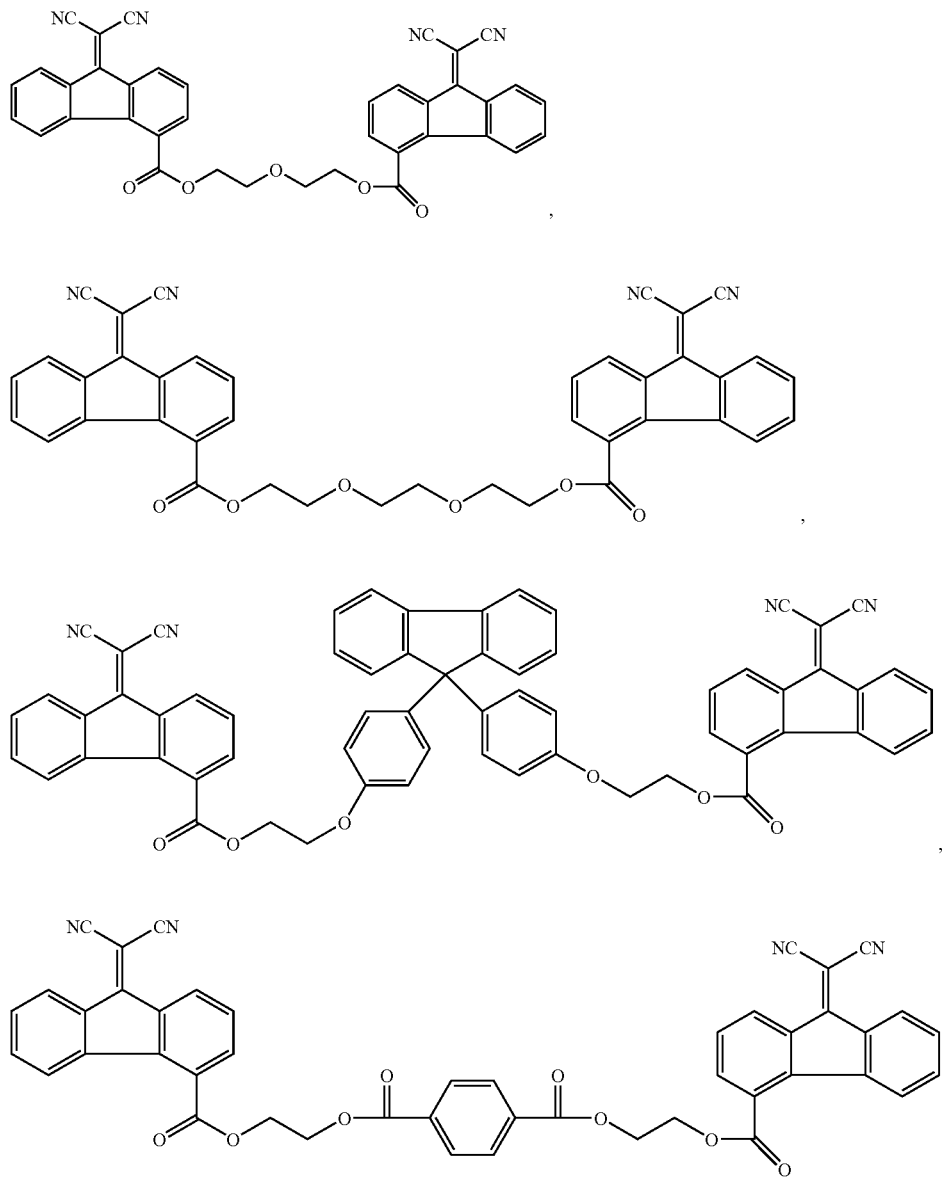

-continued
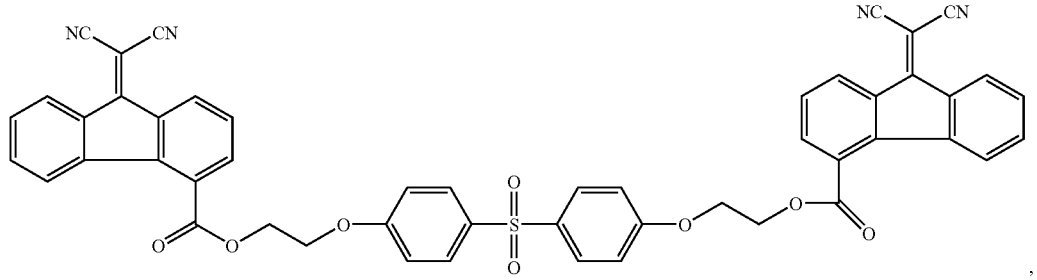
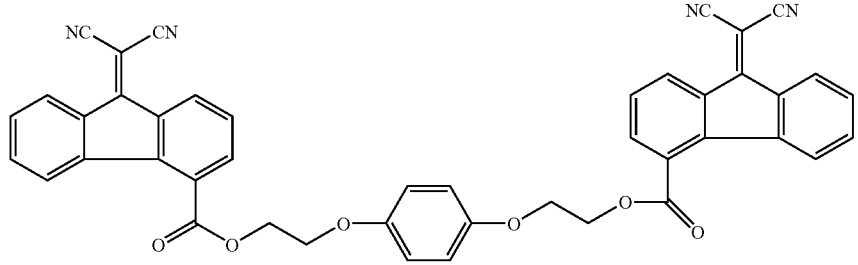
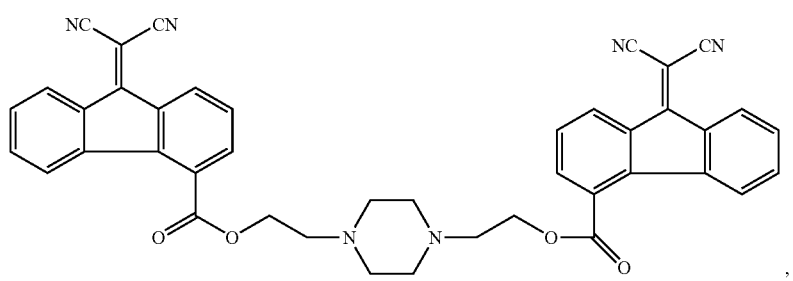
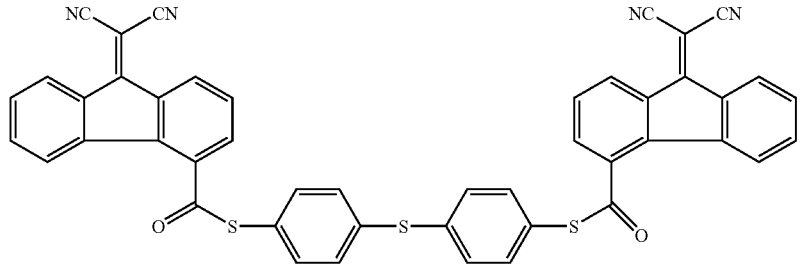
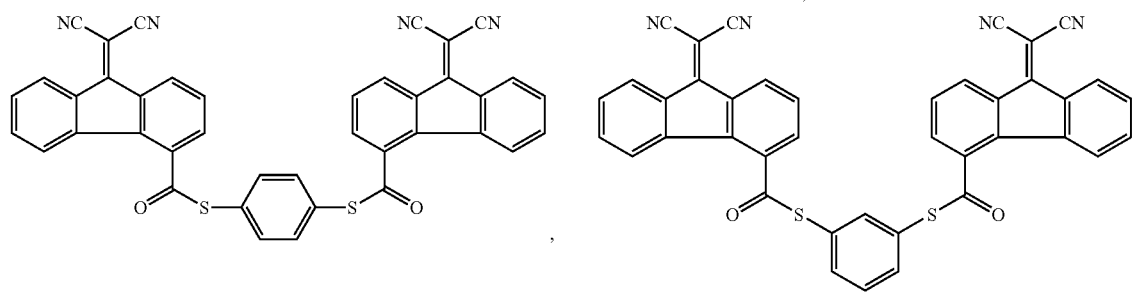
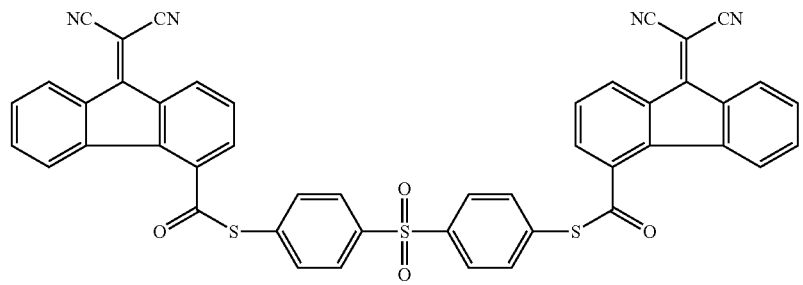

-continued

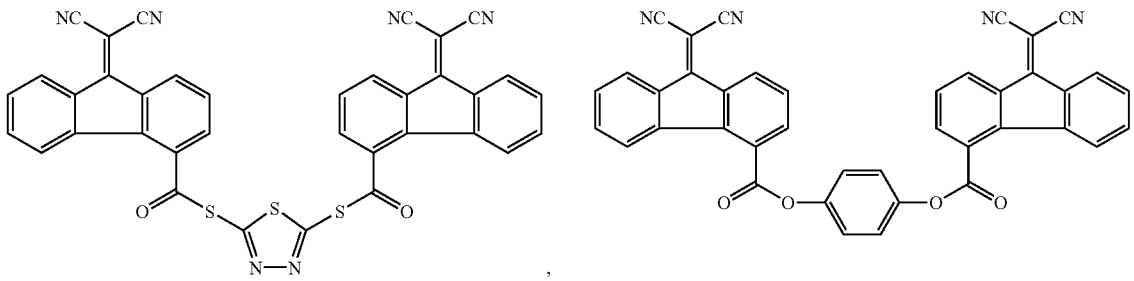

,

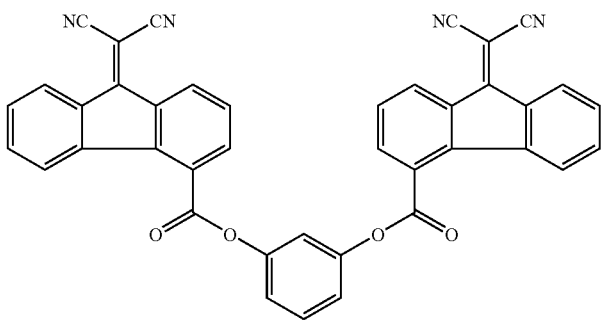

, and

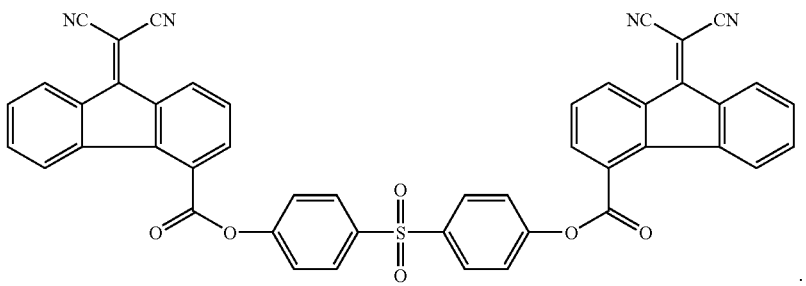

10. An electrophotographic imaging apparatus according to claim 7 wherein the photoconductive element further comprises a second charge transport material.

11. An electrophotographic imaging apparatus according to claim 10 wherein second charge transport material comprises a charge transport compound.

12. An electrophotographic imaging apparatus according to claim 7 further comprising a liquid toner dispenser.

13. An electrophotographic imaging process comprising;
(a) applying an electrical charge to a surface of an organophotoreceptor comprising an electrically conductive substrate and a photoconductive element on the electrically conductive substrate, the photoconductive element comprising
(i) a charge transport material having the formula
X-Z-X' where X and X', each independently, have the formula

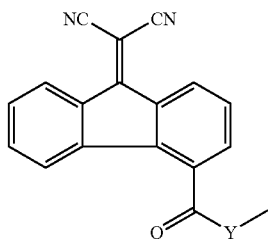

where Y is O—CH$_2$—CH$_2$—O, S, or NR$_8$ and R$_8$ is H, an alkyl group, an alkenyl group, an aromatic group, or a heterocyclic group, and Z is a linking group having the formula —(CH$_2$)$_m$—, branched or linear, where m is an integer between 1 and 30, inclusive, and one or more of the methylene groups may be replaced by O, S, C=O, Si=O, S(=O)$_2$, P(=O)$_2$, an aromatic group, a heterocyclic group, an aliphatic cyclic group, a Si(R$_1$)(R$_2$) group, a BR$_3$ group, a NR$_4$ group, a CHR$_5$ group, or a CR$_6$R$_7$ group where R$_1$, R$_2$, R$_3$, R$_4$, R$_5$, R$_6$, and R$_7$ are, each independently, H, halogen, hydroxyl, thiol, an alkoxy group, an alkyl group, an alkenyl group, an aromatic group, a heterocyclic group, or a part of a cyclic ring; and (ii) a charge generating compound.

(b) imagewise exposing the surface of the organophotoreceptor to radiation to dissipate charge in selected areas and thereby form a pattern of charged and uncharged areas on the surface;

(c) contacting the surface with a toner to create a toned image; and (d) transferring the toned image to substrate.

14. An electrophotographic imaging process according to claim 13 wherein Z comprises an aromatic group or a heterocyclic group.

15. An electrophotographic imaging process according to claim 13 wherein the charge transport material has a formula selected from the group consisting of the following:

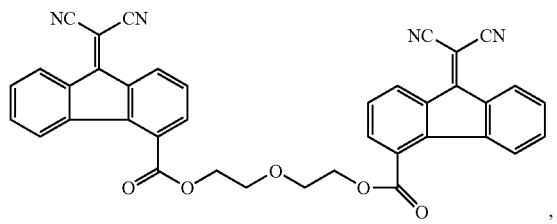

,

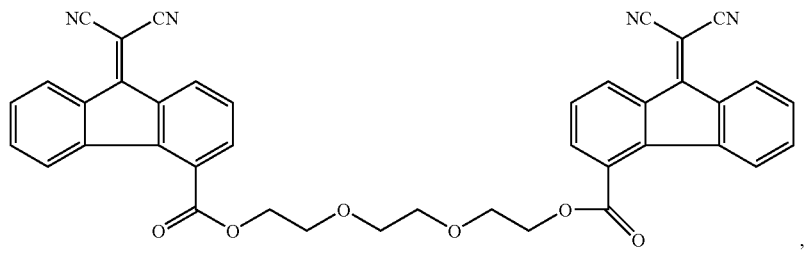

,

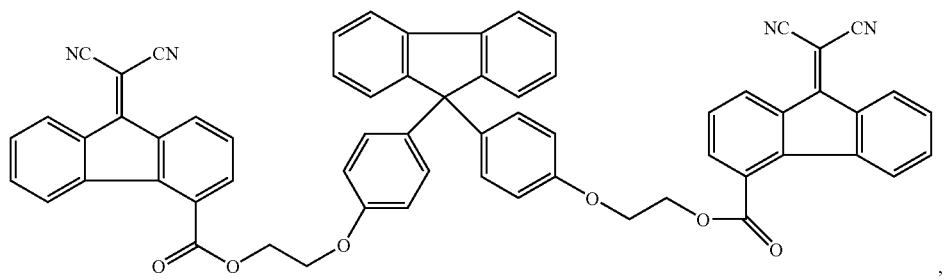

,

-continued
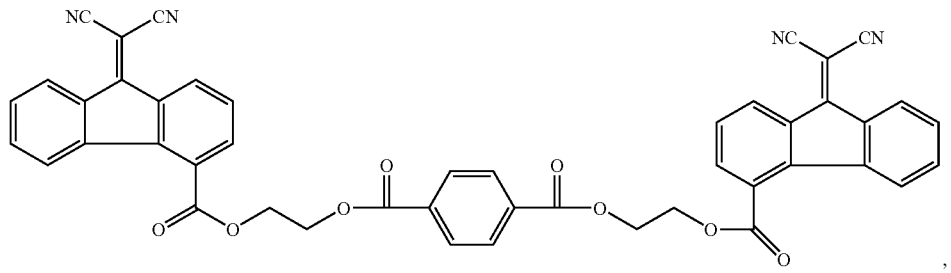
,
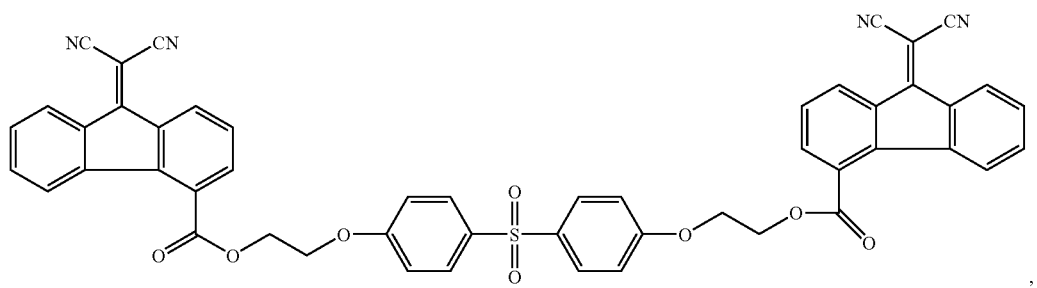
,
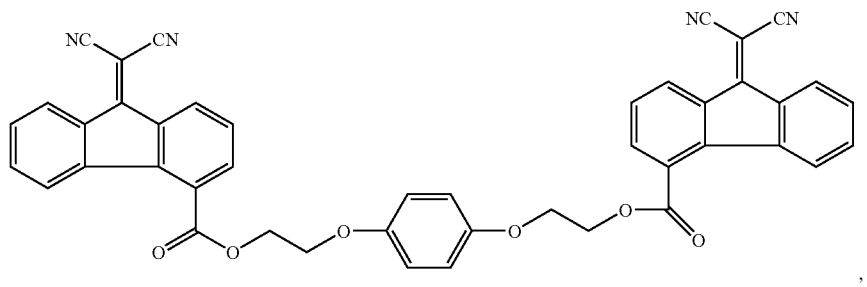
,
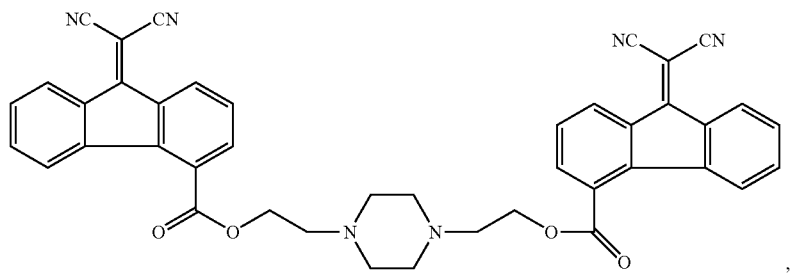
,

-continued
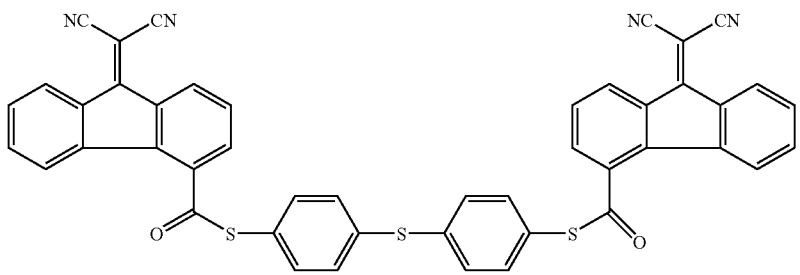
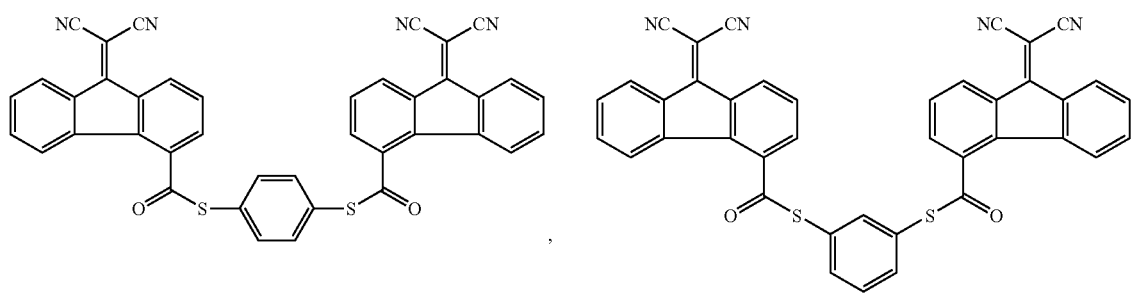
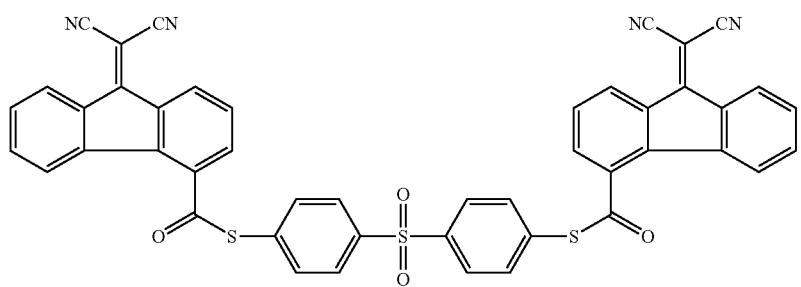
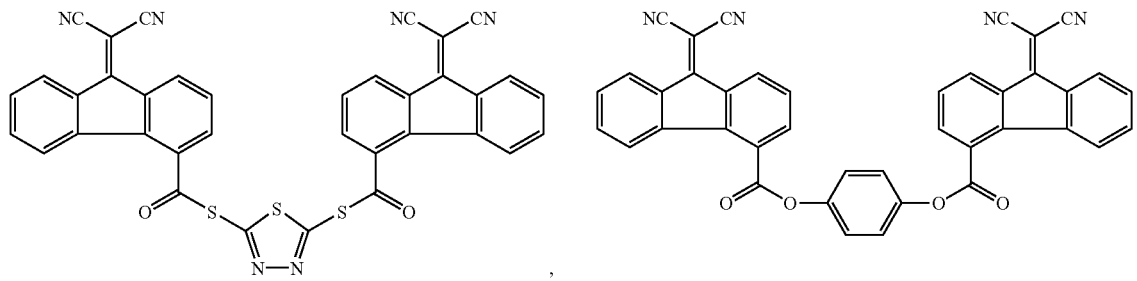
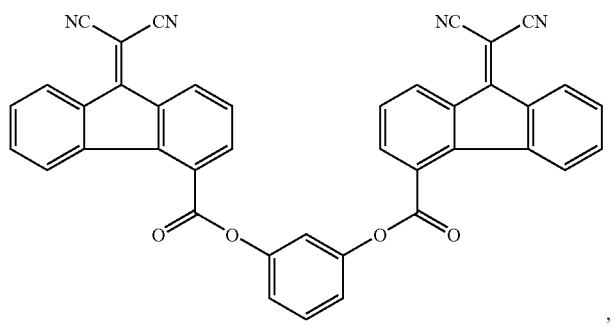
, and

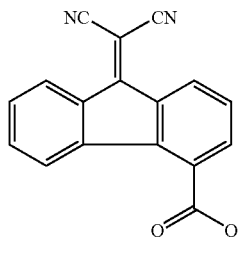
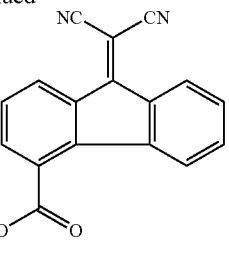

16. An electrophotographic imaging process according to claim 13 wherein the photoconductive element further comprises a second charge transport material.

17. An electrophotographic imaging process according to claim 16 wherein the second charge transport material comprises a charge transport compound.

18. An electrophotographic imaging process according to claim 13 wherein the photoconductive element further comprises a binder.

19. An electrophotographic imaging process according to claim 13 wherein the toner comprises a liquid toner comprising a dispersion of colorant particles in an organic liquid.

20. A charge transport material having the formula

X-Z-X' where X and X', each independently, have the formula

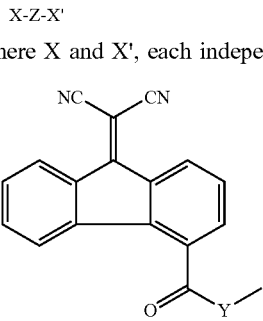

where Y is O—CH$_2$—CH$_2$—O, S, or NR$_8$ and R$_8$ is H, an alkyl group, an alkenyl group, an aromatic group, or a heterocyclic group, and Z is a linking group having the formula —(CH$_2$)$_m$—, branched or linear, where m is an integer between 1 and 30, inclusive, and one or more of the methylene groups may be replaced by O, S, C=O, Si=O, S(=O)$_2$, P(=O)$_2$, an aromatic group, a heterocyclic group, an aliphatic cyclic group, a Si(R$_1$)(R$_2$) group, a BR$_3$ group, a NR$_4$ group, a CHR$_5$ group, or a CR$_6$R$_7$ group where R$_1$, R$_2$, R$_3$, R$_4$, R$_5$, R$_6$, and R$_7$ are, each independently, H, halogen, hydroxyl, thiol, an alkoxy group, an alkyl group, an alkenyl group, an aromatic group, a heterocyclic group, or a part of a cyclic ring.

21. A charge transport material according to claim 20 wherein Z comprises an aromatic group or a heterocyclic group.

22. A charge transport material according to claim 20 wherein the charge transport material has a formula selected from the group consisting of the following:

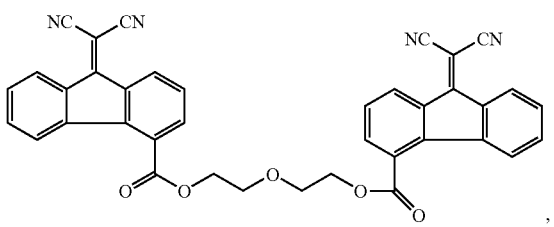

,

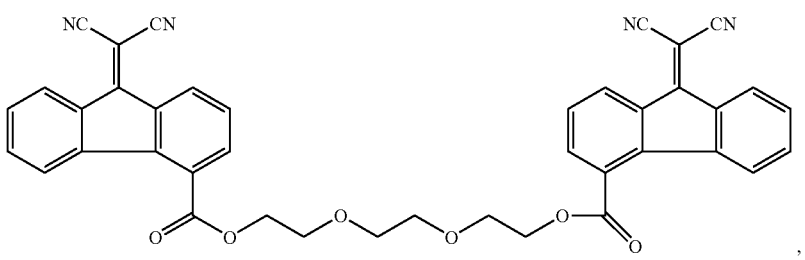

,

-continued
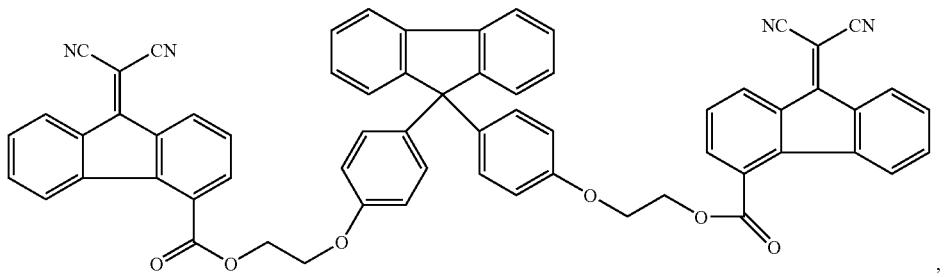
,
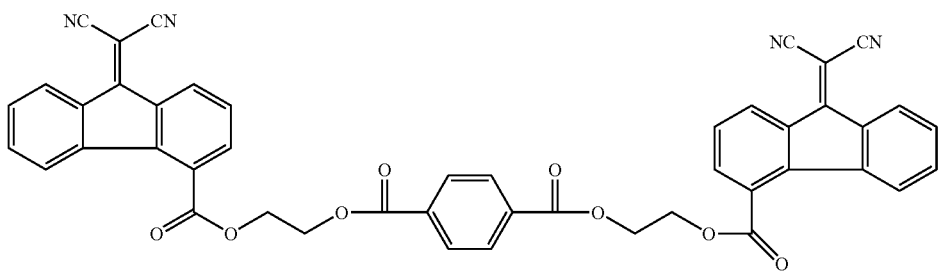
,
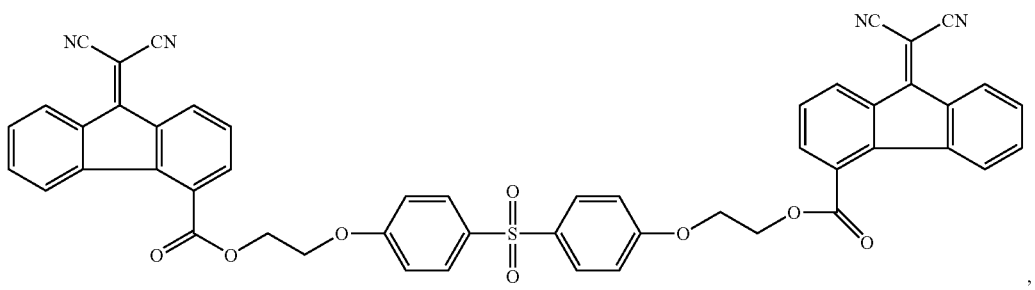
,
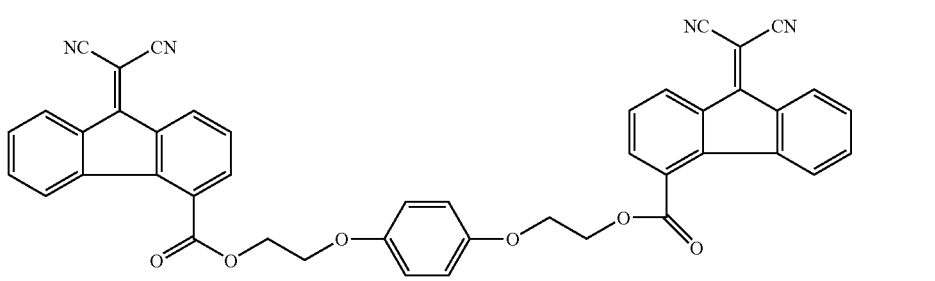
,
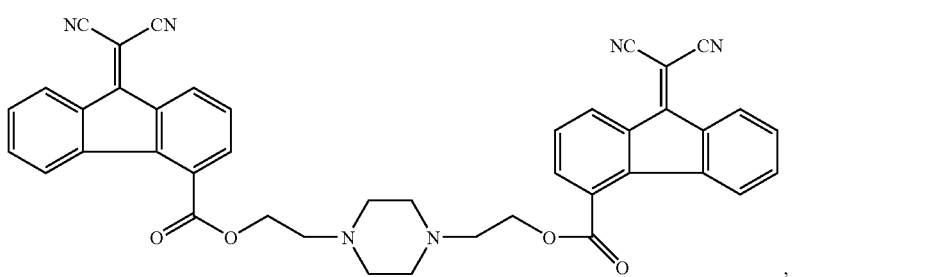
,

-continued
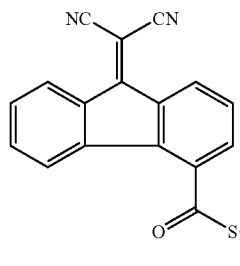 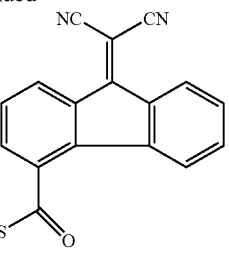,
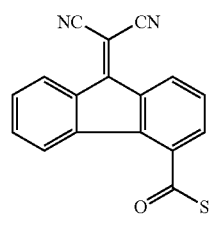, 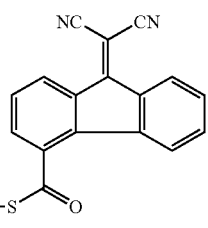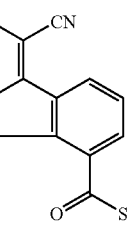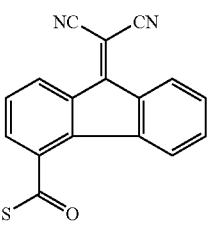,
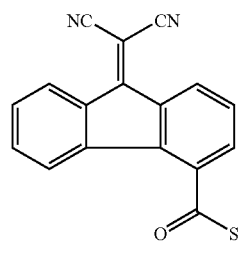,
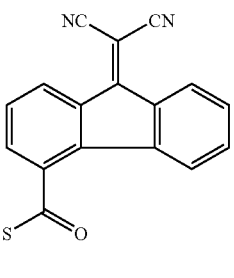, 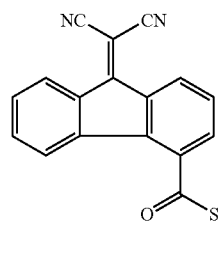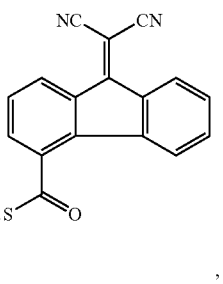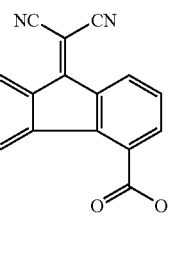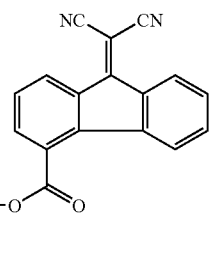,
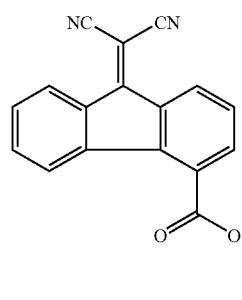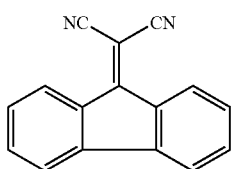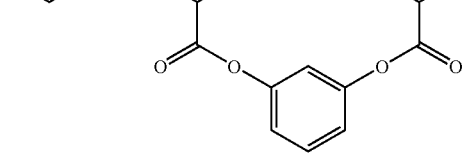
, and -continued
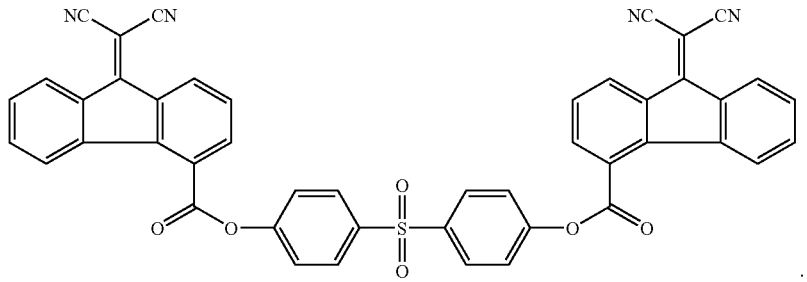
* * * * *